United States Patent
Hanebuchi

(10) Patent No.: US 9,433,353 B2
(45) Date of Patent: Sep. 6, 2016

(54) OPTICAL COHERENCE TOMOGRAPHY APPARATUS

(75) Inventor: Masaaki Hanebuchi, Aichi-ken (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 13/530,524

(22) Filed: Jun. 22, 2012

(65) Prior Publication Data
US 2012/0327423 A1   Dec. 27, 2012

(30) Foreign Application Priority Data

Jun. 23, 2011  (JP) ................. 2011-139246
Jan. 19, 2012  (JP) ................. 2012-009498

(51) Int. Cl.
*G01B 9/02*       (2006.01)
*A61B 5/00*       (2006.01)
(Continued)

(52) U.S. Cl.
CPC ............ *A61B 5/0066* (2013.01); *A61B 3/102* (2013.01); *A61B 3/1005* (2013.01); *G01B 9/02004* (2013.01); *G01B 9/02019* (2013.01); *G01B 9/02028* (2013.01); *G01B 9/02045* (2013.01); *G01B 9/02091* (2013.01); *G01N 21/4795* (2013.01); *G01B 2290/45* (2013.01)

(58) Field of Classification Search
CPC .. A61B 3/102; A61B 5/0066; G01B 5/0066; G01B 9/02019; G01B 9/02028; G01B 9/02045; G01B 9/02004; G01N 21/4795
USPC .................. 356/477–485, 491–497
See application file for complete search history.

(56) References Cited

U.S. PATENT DOCUMENTS 7,075,658 B2 *  7/2006  Izatt .................. G01B 9/02004
                                                          356/479
7,710,577 B2    5/2010  Yatagai et al.
(Continued)

FOREIGN PATENT DOCUMENTS

EP          2 314 203 A1    4/2011
JP          A-2007-298461   11/2007
(Continued)

OTHER PUBLICATIONS

Park, B. Hyle et al., "Real-time fiber-based multi-functional spectral-domain optical coherence tomography at 1.3µm," Optics Express, May 30, 2005, pp. 3931-3944. vol. 13, No. 11.
(Continued)

*Primary Examiner* — Kara E Geisel
*Assistant Examiner* — Dominic J Bologna
(74) *Attorney, Agent, or Firm* — Oliff PLC

(57) ABSTRACT

An optical coherence tomography (OCT) apparatus includes: a light source; an OCT optical system including: a first light splitter which splits light emitted from the light source into measurement and reference lights, a second light splitter which splits the measurement light into first and second beams, an optical delay path to generate an optical path length difference between the first and second beams, a scan optical system which scans the respective beams on an object to be examined in a transverse direction, a reference optical system, and a detector which receives a spectrum of composite light in which reflected lights of the first and second beams from the object, and the reference light from the reference optical system are combined; and an arithmetic controller which processes an interference signal output from the detector to obtain first and second tomographic images formed respectively by the first and second beams.

19 Claims, 9 Drawing Sheets

(51) Int. Cl.
*A61B 3/10* (2006.01)
*G01N 21/47* (2006.01)

(56) References Cited

U.S. PATENT DOCUMENTS

| | | | |
|---|---|---|---|
| 7,954,946 | B2 | 6/2011 | Murata |
| 8,472,028 | B2 | 6/2013 | Hirose |
| 8,879,070 | B2 | 11/2014 | Yasuno et al. |
| 9,025,847 | B2 | 5/2015 | Kitamura et al. |
| 2004/0036838 | A1* | 2/2004 | Podoleanu et al. ............ 351/206 |
| 2007/0236700 | A1* | 10/2007 | Yun et al. ...................... 356/491 |
| 2008/0002183 | A1* | 1/2008 | Yatagai .............. G01N 21/4795 356/73 |
| 2008/0285043 | A1* | 11/2008 | Fercher et al. ................ 356/451 |
| 2009/0059971 | A1 | 3/2009 | Atia et al. |
| 2010/0220287 | A1 | 9/2010 | Sumiya |
| 2010/0284021 | A1* | 11/2010 | Hacker .......................... 356/497 |
| 2011/0090461 | A1* | 4/2011 | Blalock ................ A61B 3/1005 351/221 |
| 2012/0120408 | A1* | 5/2012 | Yasuno et al. ................. 356/479 |
| 2012/0188555 | A1* | 7/2012 | Izatt et al. ..................... 356/479 |

FOREIGN PATENT DOCUMENTS

| | | |
|---|---|---|
| JP | 2010-029648 A | 2/2010 |
| JP | 2010-117372 A | 5/2010 |
| JP | A-2010-259698 | 11/2010 |
| JP | 2011-200635 A | 10/2011 |
| WO | WO 02/056075 A1 | 7/2002 |
| WO | WO 2006/054975 A1 | 5/2006 |
| WO | WO 2010/131531 A1 | 11/2010 |
| WO | WO 2010/134564 A1 | 11/2010 |
| WO | WO 2010/134624 A1 | 11/2010 |
| WO | 2010/143601 A1 | 12/2010 |
| WO | WO 2010/143601 A1 | 12/2010 |

OTHER PUBLICATIONS

Dhalla, Al-Hafeez, et al., "Complete complex conjugate resolved heterodyne swept source optical coherence tomography using a dispersive optical delay line: erratum," Biomedical Optics Express, Mar. 1, 2012, pp. 630-632. vol. 3, No. 3.

Extended European Search Report issued in European Patent Application No. 12173148.3 dated Mar. 4, 2013.

Nov. 24, 2015 Office Action issued in Japanese Patent Application No. 2012-009498.

* cited by examiner

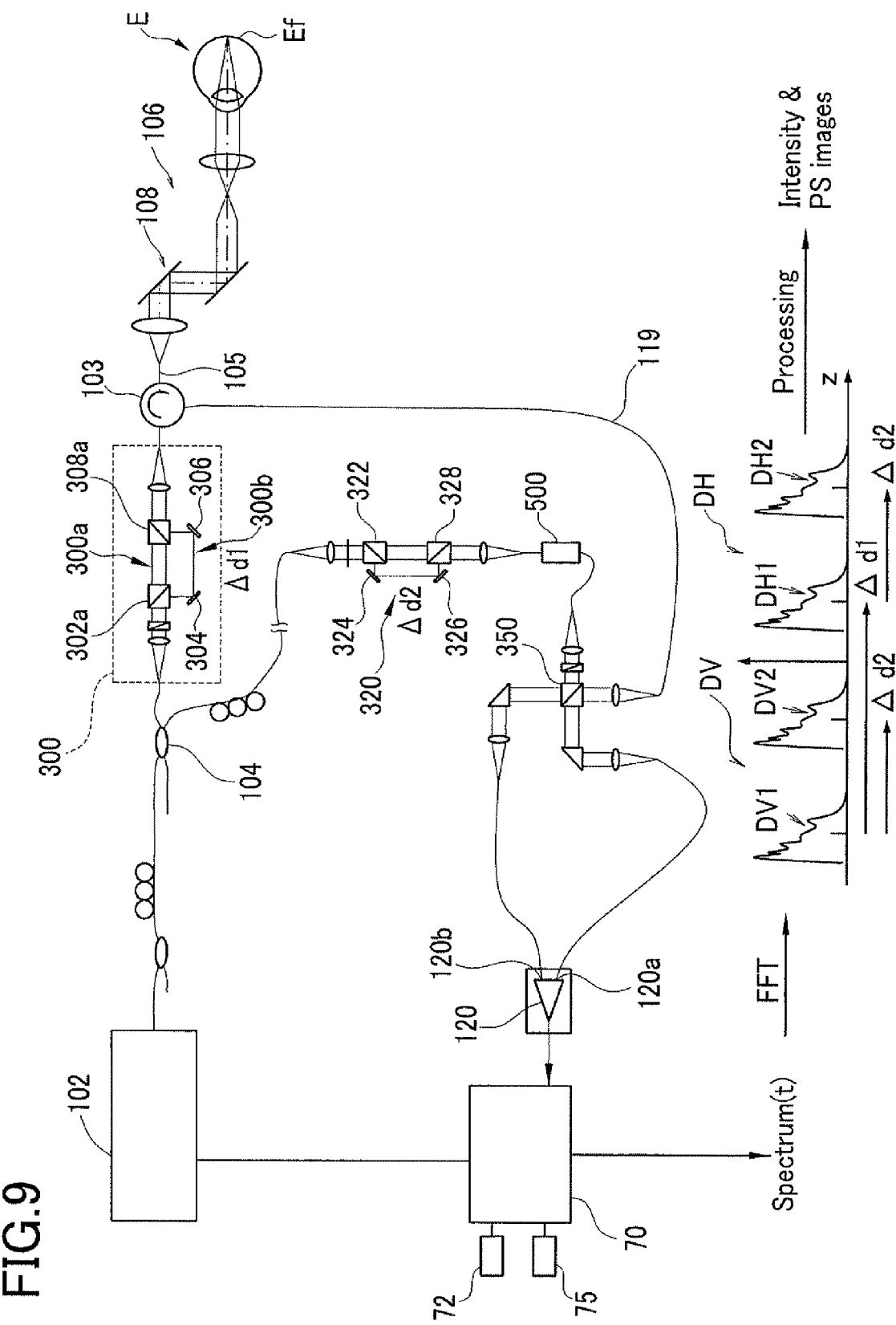

$$\begin{cases} p1 \perp p2 \\ p1'(z) \perp p2'(z) \\ \theta 1 = \theta 2 \end{cases}$$

OPTICAL COHERENCE TOMOGRAPHY APPARATUS

CROSS-REFERENCE TO RELATED APPLICATIONS

This application is based upon and claim's the benefit of priority from the prior Japanese Patent Applications No. 2011-139246, filed Jun. 23, 2011, and No. 2012-009498; filed Jan. 19, 2012, the entire contents of which are incorporated herein by reference.

BACKGROUND OF THE INVENTION

1. Technical Field

The invention relates to an optical coherence tomography apparatus which measures an object to be examined through the use of optical interference between measurement and reference lights.

2. Background Art

A first example of optical coherence tomography apparatuses which measures an object to be examined through the use of optical interference between measurement and reference lights is a two-beam optical coherence tomography apparatus wherein a measurement light is split into a plurality of beams (see Patent Documents 1 and 2).

According to the apparatus, the measurement light is split into two different beams, and a first composite light obtained by combining a reflected light of the first beam from an object to be examined with a reference light is received by a first spectrometer and a second composite light obtained by combining a reflected light of the second beam from the object to be examined with the reference light is received by a second spectrometer. Then, signals respectively output from the spectrometers are processed to obtain a first tomographic image formed by the first beam and a second tomographic image formed by the second beam.

The technical complexity of the apparatus, wherein two spectrometers are provided and the light is split into two fluxes by polarization, is desirably to be improved for practical use.

A known OCT apparatus is Fourier domain OCT wherein a spectral signal, in which interference signals of different wavelengths are combined, is obtained.

A second example of the apparatus is a polarization sensitive OCT (PS-OCT) which is designed to measure polarization properties of an object to be examined (see Non-Patent Document 1). The apparatus disclosed in Non-Patent Document 1 includes: an EO modulator (polarization modulator, electro-optic modulator) to scan and sequentially modulate at the same time a polarization states of beam emitted from a light source in a transverse direction of the measurement light; and two light detectors to measure at once vertical polarization components and horizontal polarization components included in spectral components. The apparatus thus structurally characterized obtains the polarization properties based on the spectral component including the vertical polarization component and the horizontal polarization component in a first polarization state of the beam and the spectral component including the vertical polarization component and the horizontal polarization component in a second polarization state of the beam.

To obtain a plurality of tomographic images of a site to be photographed, the conventional OCT was required to extract a plurality of tomographic images from tomographic images sequentially obtained at a given frame rate or have a plurality of detection systems.

In the conventional polarization sensitive OCT, it was necessary to sequentially change the beam polarization states to obtain the polarization properties using Jones vector parameters. The EO modulator used to change the polarization states is an expensive device, which is a reason why the PS-OCT is still commercially unavailable.

RELATED ART DOCUMENTS

Patent Documents

Patent Document 1: WO2010/143601
Patent Document 2: JP-A-2010-259698
Patent Document 3: JP-A-2007-298461
Non-Patent Document 1: B. Hyle Park, M. C. Pierce, Barry Cense, S. H Yun, B. E. Bouma, J. F. de Boer, "Real-time fiber-based multi-functional spectral domain optical coherence tomography at 1.3 µm", Optics Express, Vol 13('05), pp 3931-3944

SUMMARY

The invention has a purpose to provide an optical coherence tomography apparatus wherein at least one of the aforementioned technical disadvantages of the conventional optical coherence tomography apparatuses has been overcome.

The invention has another purpose to provide an optical coherence tomography apparatus wherein tomographic images can be smoothly obtained in a simplified manner.

Means of Solving the Problems

To achieve the above purposes, one aspect of the present invention provides an optical coherence tomography apparatus including: a light source; an optical coherence tomography optical system including: a first light splitter which splits light emitted from the light source into a measurement light and a reference light, a second light splitter which splits the measurement light into a first beam and a second beam independent from each other, an optical delay path provided in an optical path of the measurement light to generate an optical path length difference between the first beam and the second beam, a scan optical system which scans the respective beams on an object to be examined in a transverse direction, a reference optical system, and a detector which receives a spectrum of composite light in which a reflected light of the first beam from the object to be examined, a reflected light of the second beam from the object to be examined, and the reference light from the reference optical system are combined; and an arithmetic controller which processes an interference signal output from the detector to obtain a first tomographic image formed by the first beam and a second tomographic image formed by the second beam.

According to the invention, tomographic images can be smoothly obtained in a simplified manner.

BRIEF DESCRIPTION OF THE DRAWINGS

FIG. 9 is a diagram for describing the structural elements of the apparatus according to Example 2 of the embodiment;

DESCRIPTION OF EMBODIMENTS

First Embodiment

Figure 1:
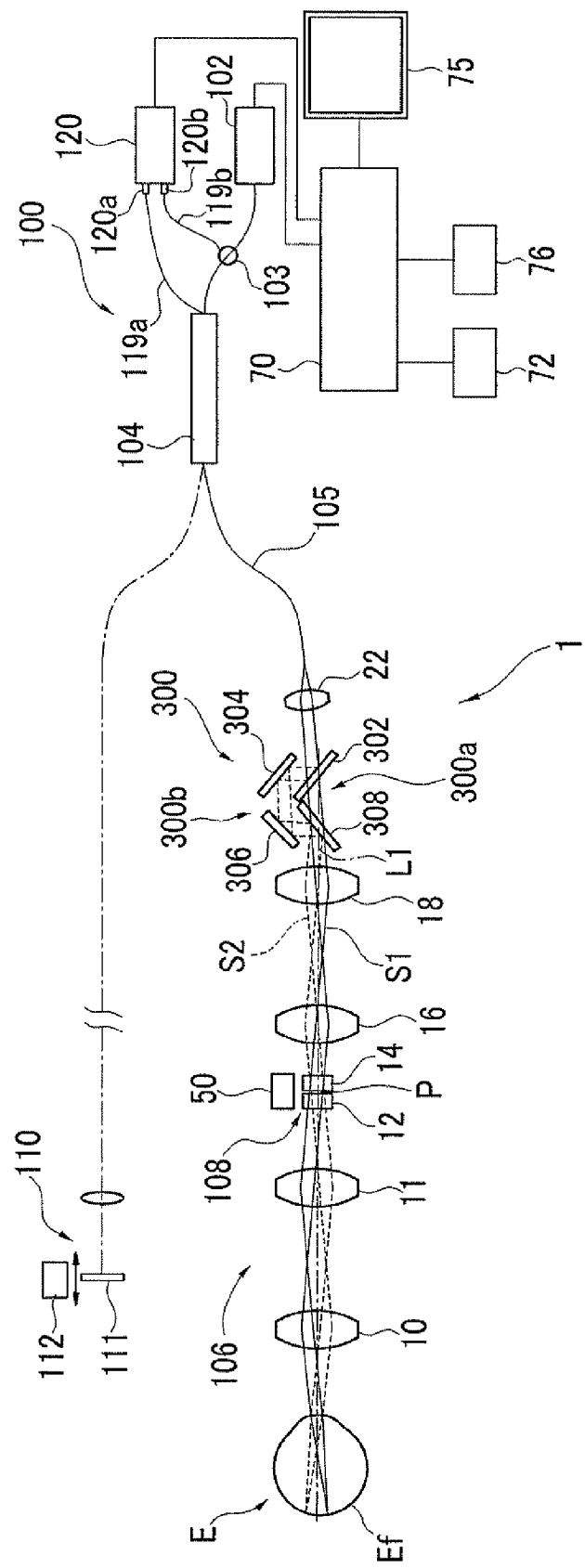
FIG. 1 schematically illustrates structural elements of an optical coherence tomography apparatus according to an embodiment of the invention (Example 1)

An optical coherence tomography apparatus according to a first embodiment of the invention is hereinafter described. FIG. 1 schematically illustrates structural elements of an optical coherence tomography apparatus according to this embodiment.

An optical coherence tomography (OCT) apparatus 1 basically configured as Swept Source-OCT (SS-OCT) includes: a wavelength variable light source 102, an interference optical system (OCT optical system) 100, and an arithmetic controller (hereinafter, controller) 70. The wavelength variable light source 102 changes the wavelength of an outgoing light. The interference optical system (OCT optical system) 100 obtains a spectral interference signal of a reference light and a reflected light from an object to be examined (for example, an eye E). The controller 70 obtains a depth profile by processing the obtained interference signal. The OCT apparatus 1 scans light on the object to be examined and obtains a tomographic image based on the depth profiles obtained at different positions. Examples of the object to be examined are body parts such as eye (for example, anterior segment or fundus) and skin, however, the object to be examined is not necessarily limited to such biological objects.

In the OCT apparatus 1, light from the light source 102 is split into a measurement light and a reference light by a coupler (splitter) 104, and the measurement light is split by a light splitter 302 into two independent beams. An optical delay path 300 generates a difference in optical path length between the split two beams. These beams are irradiated simultaneously on different sites so that the object to be examined is scanned by an optical scanner 108.

The beams are reflected from the object to be examined, and resulting reflected lights are combined with a reference light emitted from a reference optical system 110, and the composite light (interference light) is received by a detector 120. Then, a corresponding interference signal is input to the arithmetic controller (CPU) 70. After the wavelength is changed by the wavelength variable light source 102, spectral data of the interference signals formed by the composite lights of different wavelengths is input to the arithmetic controller (CPU) 70 and signal-processed by the controller 70.

The controller 70 processes the interference signal output from the detector 120 to obtain a first tomographic image formed by a first beam and a second tomographic image formed by a second beam.

The spectral data input to the controller 70 is rewritten in the form of function of wavelength $\lambda$ to be transformed into an equal-interval function $I(k)$ for wave number k $(=2\pi/\lambda)$. The controller 70 performs Fourier transform to the interference signals of the respective beams relating to the same site and then calculates a phase variation based on Doppler shift frequencies (described in detail later). The controller 70 calculates a moving speed of the object to be examined based on the phase variation to obtain a flow rate (moving speed of the object to be examined). The controller 70 averages the flow rates at different spots to measure an average flow rate in a large area (average moving speed of the object to be examined).

The controller 70 processes amplitudes and phases of the signals in a signal amplitude processing step and a signal phase processing step to obtain a tomographic image and a Doppler image. The controller 70 displays the obtained images on a monitor 75 (image display unit).

In FIG. 1, the optical delay path 300 is provided in a measurement optical path and includes a light splitter 302 and an optical combiner 308. The light splitter 302 splits the measurement light emitted from the light source 102 into a reference optical path 300a (first measurement optical path) and a detour optical path 300b (a second measurement optical path). The optical combiner 308 combines the reference optical path 300a and the detour optical path 300b (see FIG. 1).

An optical path length difference is generated by the optical delay path 300 so that the tomographic image obtained by one of the beams is formed in a front-side part and the tomographic image obtained by the other beam is formed in a rear-side part in a tomographic image capturing range in a depth direction.

A scan optical system of the OCT apparatus 1 scans the beams on the same position of the object to be examined, for example, the scan optical system scans two beams in a beam-splitting direction of the two beams. The controller 70 processes the interference signal output from the detector 120 to obtain two tomographic images of the same site captured at different points of time and measure a phase variation with time of the same site. Accordingly, the Doppler measurement which uses at least two beams can be performed in a simplified manner.

The scan optical system of the OCT apparatus 1 may scan the beams on different positions of the object to be examined, for example, the scan optical system scans two beams in a direction different to the beam-splitting direction. The controller 70 processes the interference signal output from the detector 120 to obtain a first tomographic image and a second tomographic image at different scan positions. Accordingly, a plurality of tomographic images can be obtained at the same time in a simplified manner.

The wavelength variable light source 102 may be a wavelength variable light source wherein an instantaneous emission line width is narrow, wherein two tomographic images having different optical path lengths are obtained with an almost equal interference intensity and separately from each other. Further, the wavelength variable light source ensures an image capturing range including the first and second tomographic images separate from each other in the depth direction.

Hereinafter, Examples according to the invention are described in detail referring to the drawings.

Example 1

An optical coherence tomography apparatus used in Example 1 is the OCT apparatus 1 illustrated in FIG. 1 similar to the apparatus described in the embodiment, wherein the object to be examined is a fundus of an eye.

The OCT apparatus 1 includes the interference optical system (OCT optical system) 100, the arithmetic controller (CPU) 70, a memory 72, and a monitor 75. The apparatus further includes other devices, though not illustrated in the drawing, such as a front observation optical system and a fixation target projecting system.

The SS-OCT is employed in the OCT optical system 100, a wavelength variable light source capable of high-speed change of an emission wavelength with less time (wavelength scan light source) is used as the light source 102, and a balanced detector including, a first photo detector 120a and a second photo detector 120b, for example, is used as the detector 120. The photo detectors are each a point sensor including just one photo detecting device, an example of which is avalanche photo diode.

The light source 102 includes, for example, a laser medium, a resonator, and a wavelength selective filter. Examples of the wavelength selective filter are a combination of a diffraction grating and a polygonal mirror, and a filter in which Fabry-Perot etalon is used.

Example 1 uses a tunable laser supplied by AXSUN TECHNOLOGIES INC. which is a light source having a short instantaneous emission line width and a short cavity length (for example, $\lambda c=1060$ nm, $\Delta\lambda=110$ nm, $\delta\lambda=0.055$ nm, cavity length up to 14 mm). An example of the wavelength variable light source is disclosed in US Patent Publication No. 2009/0059971.

The OCT optical system 100 splits light emitted from the light source 102 into a measurement light and a reference light using the coupler (splitter) 104. A circulator 103 guides the light emitted from the light source 102 to the coupler 104 and guides the light from the coupler 104 to the detector 120.

The OCT optical system 100 guides the measurement light using a measurement optical system 106 to the fundus Ef of the eye E and guides the reference light to the reference optical system 110. The OCT optical system 100 makes the detector (photo detector) 120 receive an interference light obtained by combining the measurement light reflected from the fundus Ef with the reference light.

The measurement optical system 106 includes an optical fiber 105, a collimator lens 22, the optical delay path 300, a focus lens 18, a collimator lens 16, the optical scanner 108, a relay lens 11, and an objective lens 10. To separate a first measurement light S1 and a second measurement light S2, the collimator lens 22 is positioned so that an optical axis of the lens 22 is tilting relative to an optical axis L1 of the measurement optical system 106. The focus lens 18 is movable in an optical axis direction for focus adjustment of the object to be examined.

The optical delay path 300 includes a light splitter 302, a first light reflector 304, a second light reflector 306, and an optical combiner 308, wherein the measurement light is split into two optical paths, and an optical path length of one of the measurement lights is delayed relative to the other measurement light.

Examples of the light splitter 302 and optical combiner 308 are; half mirror, beam splitter such as a polarization beam splitter, and a dichroic mirror. When, for example, the polarization beam splitter is used, the light splitter 302 splits the light from the light source into a polarized light S and a polarized light P to transmit one of the polarized lights therethrough and reflect the other polarized light. The optical combiner 308 combines the light split into the polarized light S and the polarized light P. The first light reflector 304 and the second light reflector 306 are each, for example, an optical device such as a total reflection mirror or a prism. Describing an optical layout of the optical devices constituting the optical delay path 300, the optical devices may be provided distant from one another as shown in FIG. 1, or may be integrally provided by, for example, a prism.

The light splitter 302 splits the light from the light source 102 into two different lights. For example, one of the lights entering from the light source 102 is transmitted through, while the other light is reflected by the light splitter 302. The first light reflector 304 and the second light reflector 306 reflect one of the lights split by the light splitter 302 so that the light thereby reflected returns to the optical combiner 308. The optical combiner 308 combines the split lights. For example, one of the split lights is transmitted through, while the other light is reflected. These lights advance toward the fundus Ef.

The measurement light from the optical fiber 105 is split by a first optical path 300a (a reference optical path) and a second optical path 300b (a detour optical path) provided in the optical delay path 300 to generate the first measurement light S1 and the second measurement light S2. Because the second measurement optical path 300b has an optical path longer than that of the first measurement optical path 300a, the second measurement light S2 is optically delayed relative to the first measurement light S1 (an optical path length difference). A reflected light of the measurement light from the fundus Ef is similarly delayed.

In the above-described structure, the first measurement light S1 and the second measurement light S2 which transmitted through the optical delay path 300 are converged by the focus lens 18 and then converted into a collimated beam by the collimator lens 16, and its reflection direction is changed by the optical scanner 108 including a galvano mirror 14 and a galvano mirror 12. The light thus deflected by the optical scanner 108 is once converged by the relay lens 11 and then converted into a collimated beam by the objective lens 10. Then, the collimated beam entering through the eye E is irradiated on the fundus Ef.

The optical scanner 108 makes the measurement light scan the fundus Ef in X-Y direction (transverse direction). The optical scanner 108 is located at a position substantially conjugate with a pupil. The optical scanner 108 is, for example, two galvano mirrors 12 and 14 wherein light reflection angles are arbitrarily adjusted by a drive mechanism 50.

A luminous flux emitted from the light source 102 accordingly changes its reflection (travelling) direction, and the luminous flux is irradiated on the fundus for scan in any arbitrary directions. Examples of the optical scanner 108 are a reflector mirror (a galvano mirror, a polygonal mirror, a resonant scanner), and an acousto-optic modulator (AOM) which changes a light travelling (deflection) direction.

A principal ray of the first measurement light S1 and a principal ray of the second measurement light S2 intersect with each other at a pupil conjugate position P (optical scanner). The principal rays that intersected with each other on the pupil finally arrive at the fundus Ef. The first measurement light S1 and the second measurement light S2 are spatially split with a suitable interval A therebetween in a scan direction. Thus, two probe beams including the first measurement light S1 and the second measurement light S2 are formed with the interval A therebetween in the scan direction.

The controller 70 drives the optical scanner 108 to make the first measurement light S1 and the second measurement light S2 scan the fundus Ef in a direction perpendicular to the depth direction of the fundus Ef (transverse direction). The controller 70 adjusts the scan direction of the optical scanner 108 so that the first measurement light S1 and the second measurement light S2 split from each other on a scan line are irradiated at the same time on different positions of a scan line of the fundus Ef.

A back scattered light of the first measurement light S1 and the second measurement light S2 (reflected lights) from the fundus Ef travels through the objective lens 10 to the focus lens 18 and arrives at the optical delay path 300. Then, the back scattered light is split into two lights by the optical combiner 308 and then combined by the light splitter 302. The resulting signal returns to the coupler 104 as an object beam and combined with the reference light for optical interference.

The reference optical system 110 generates the reference light to be combined with a reflected light obtained when the measurement light is reflected from the fundus Ef. The reference optical system 110 may be of Michelson type or Mach-Zehnder type. The reference optical system 110 includes, for example, a reflection optical system (for example, a reference mirror), wherein the light from the coupler 104 is reflected by the reflection optical system to be returned to the coupler 104 and then guided to the detector 120. Another example of the reference optical system 110 includes a transmission optical system (for example, an optical fiber), wherein the light from the coupler 104 is not returned but is transmitted through the transmission optical system to be directly guided to the detector 120.

For adjustment of the different optical path lengths of the measurement light and the reference light, the apparatus moves at least a part of the optical devices provided in the OCT optical system 100 in the optical axis direction. For example, the reference optical system 110 moves the optical devices provided in the reference optical path (for example, a reference mirror 111) to adjust the different optical path lengths of the measurement light and the reference light. For example, the drive mechanism 112 is driven to move the reference mirror 111 in the optical axis direction. A technical configuration for changing the different optical path lengths may be provided in the measurement optical path of the measurement optical system 106. In that case, the optical devices provided in the measurement optical path (for example, an end portion of the optical fiber) are moved in the optical axis direction.

An interference signal light in which the measurement and reference lights are combined is bifurcated by the coupler 104 into an optical path on the side of an optical fiber 119a and an optical path on the side of an optical fiber 119b. The first photo detector 120a detects the interference signal light having passed through the optical fiber 119a. The second photo detector 120b detects the interference signal light passed through the optical fiber 119b by way of the circulator 103. The interference signal lights received by the first and second photo detectors 120a and 120b respectively include an interference signal light corresponding to the first measurement light S1 and an interference signal light corresponding to the second measurement light S2.

After an emission wavelength is changed by the light source 102, a corresponding interference signal light is received by the detector 120 as a spectral interference signal light. The spectral interference signal output from the detector 120 is fetched by the controller 70, and a depth profile is formed based on the spectral interference signal.

The detector (balanced detector) 120 obtains a difference between the interference signals from the first photo detector 120a and the second photo detector 120b to remove any unwanted noise included in the interference signals. The controller 70 drives the optical scanner 108 to make the measurement light scan the fundus Ef in the transverse direction. The controller 70 arranges the depth profiles obtained from different scan positions to form a tomographic image of the fundus.

Figure 2:
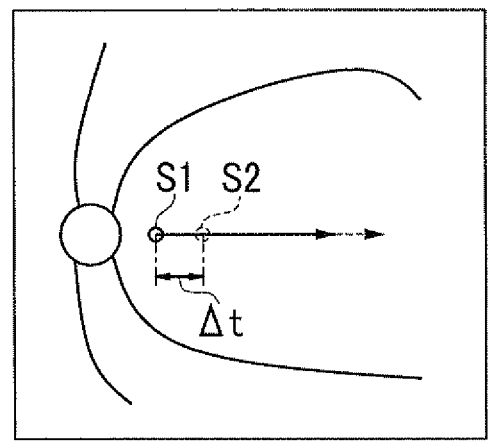
FIG. 2 illustrates an example of a scanning position on fundus, wherein two beams are scanning the fundus in a beam-splitting direction.
Figure 3:
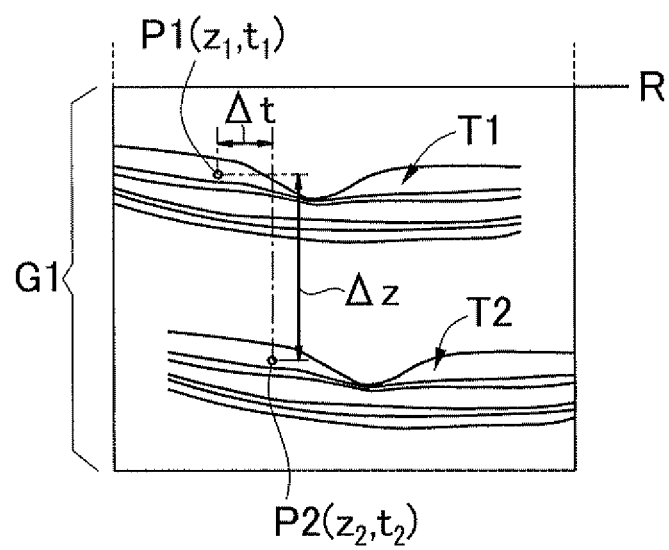
FIG. 3 illustrates a tomographic image obtained by such a dual scan as illustrated in FIG. 2.

FIG. 2 illustrates an example of the scan position on the fundus, wherein two beams are irradiated for scan in a beam-splitting direction. FIG. 3 illustrates a tomographic image obtained by such a dual scan as illustrated in FIG. 2. Though a tomographic image data obtained by Fourier analysis generally includes a real image and a mirror image, the image of FIG. 3 is obtained by extracting a real image alone. A depth position R is a depth position where the optical path lengths of the measurement and reference lights are equal, and an image capturing region G1 is a region behind the depth position R.

A tomographic image T includes a first tomographic image T1 and a second tomographic image T2. The first tomographic image T1 is formed by interference between the first measurement light S1 and the reference light, and the second tomographic image T2 is formed by interference between the second measurement light S2 and the reference light.

In the image capturing region G1, the first tomographic image T1 based on the first measurement light S1 is formed in a front-side region, while the second tomographic image T2 based on the second measurement light S2 is formed in a rear-side region. The image capturing positions thus different in the depth direction are caused by the different optical path lengths of the first measurement light S1 and the second measurement light S2. The first tomographic image T1 and the second tomographic image T2 are obtained by irradiating the respective measurement lights on different positions of the fundus Ef in the scan direction.

In FIG. 3, a point P1 (z1, t1) on the first tomographic image T1 and a point P2 (z2, t2) on the second tomographic image T2 are points of the same site in the depth and lateral directions. A shift amount $\Delta z$ of the tomographic image in the depth direction corresponds to the optical path length difference between the first and second measurement lights, which is a known shift amount. For example, the shift amount $\Delta z$ is calculated per pixel. The two points and the shift amount have a relationship expressed by $z1=z2+\Delta z$.

A shift amount $\Delta t$ of the tomographic image in the lateral direction results from an irradiation difference between the first and second measurement lights, which is a known shift amount. For example, the shift amount $\Delta t$ is calculated per pixel. The two points and the shift amount have a relationship expressed by $t2=t1+\Delta dt$. The shift amount $\Delta t$ is calculated by optical simulation. Further, the shift amount $\Delta t$ is calculated through image processes as a shift amount between the first and second tomographic images.

The controller 70 measures a moving speed of blood in a blood vessel by obtaining a phase variation at positions of the same site using the first tomographic image T1 and the second tomographic image T2.

<Operational Expressions for Obtaining Phase Variation and Flow Rate>

A phase Φ1 (z1, t1) and a phase Φ2 (z2, t2) at the points P1 (z1, t1) and P2 (z2, t2) are expressed by the following operational expression.

$$\Phi_{1,n}(z_1, t_1) = \arctan\left(\frac{\text{Im}(\tilde{I}_{1,n}(z_1))}{\text{Re}(\tilde{I}_{1,n}(z_1))}\right),$$ (Ex. 1)

$$\Phi_{2,n}(z_2, t_2) = \Phi_{1,n}(z + \Delta z, t + \Delta t) =$$
$$\arctan\left(\frac{\text{Im}(\tilde{I}_{2,n}(z_2, t_2))}{\text{Re}(\tilde{I}_{2,n}(z_2, t_2))}\right) = \arctan\left(\frac{\text{Im}(\tilde{I}_{1,n}(z + \Delta z, t + \Delta t))}{\text{Re}(\tilde{I}_{1,n}(z + \Delta z, t + \Delta t))}\right)$$

$$\tilde{I}_{1,n}(z)$$ (Ex. 2)

This operational expression 2 expresses a complex scattering intensity obtained by subjecting spectrum to fast Fourier transform for wave number k, and its relationship with a normal OCT intensity expressed by the following operational expression 3 is expressed by the following operational expression 4.

$$I_{1,n}(z)$$ (Ex. 3)

$$I_{1,n}(z) = \sqrt{(\text{Re}(\tilde{I}_{1,n}(z)))^2 + (\text{Im}(\tilde{I}_{1,n}(z)))^2}.$$ (Ex. 4)

Im represents an imaginary part of the complex number, and Re represents a real part of the complex number. n=1 to N−1, where a point is measured by Ascan N number of times.

The phase variation Δφ (z, Δt) is expressed by the following operational expression 5.

$$\Delta\Phi_n(z,\Delta t) = \Phi_{1,n}(z_1,t_1) - \Phi_{2,n}(z_2,t_2) + \Phi_0$$ (Ex. 5)

The φ0 represents a motion of the whole sample or an initial phase difference. Then, the following operational expression is obtained:

$$V(z) = \frac{\lambda}{4n\pi\Delta t(N-1)\cos\alpha} \sum_{n=1}^{N-1} \Delta\Phi_n(z, \Delta t)$$ (Ex. 6)

where α is an angle of the measurement light with bloodstream V(z).

The above operational expression obtains an average value in the lateral direction, however, may obtain an average value in the optical axis direction. To calculate the angle α, a direction of the blood vessel is additionally obtained from a normal scattering intensity OCT image.

According to the description given so far, the measurement light is split into two beams, however, may be split into three or more beams.

Figure 4:
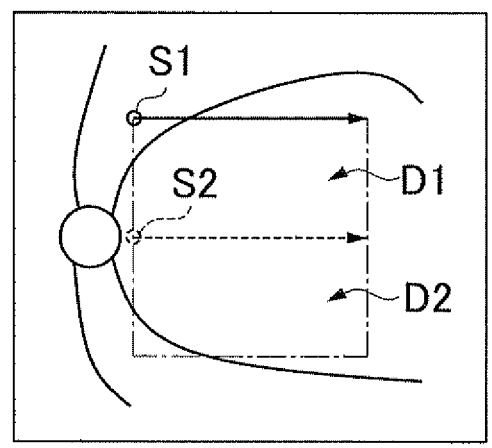
FIG. 4 illustrates an example of a scanning position on fundus, wherein two beams are scanning the fundus in a direction different to the beam-splitting direction.

The Doppler measurement mode and a normal image capturing mode for capturing tomographic images may be switchingly changed. When the normal image capturing mode is set by manipulating a mode-change switch, the controller 70 controls the optical scanner 108 to make the measurement lights scan the fundus Ef in a direction different to the beam-splitting direction of the first and second measurement lights (preferably, a direction orthogonal to the beam-splitting direction) (see FIG. 4).

Because a scan region on the fundus is divided into different regions by the two measurement lights, and tomographic images are respectively obtained for these scan regions (see FIG. 5), the tomographic images can be smoothly obtained for any desired number of scan regions. According to the method, a plurality of tomographic images can be obtained at once in a simplified manner, whenever necessary.

For example, the controller 70 can smoothly obtain a three-dimensional tomographic image by making the measurement lights two-dimensionally scan different sites of the fundus. For example, the first measurement light S1 two-dimensionally scans a rectangular region D1 on the fundus Ef, and the second measurement light S2 two-dimensionally scans a rectangular region D2 on the fundus Ef.

Example 2

Figure 6:
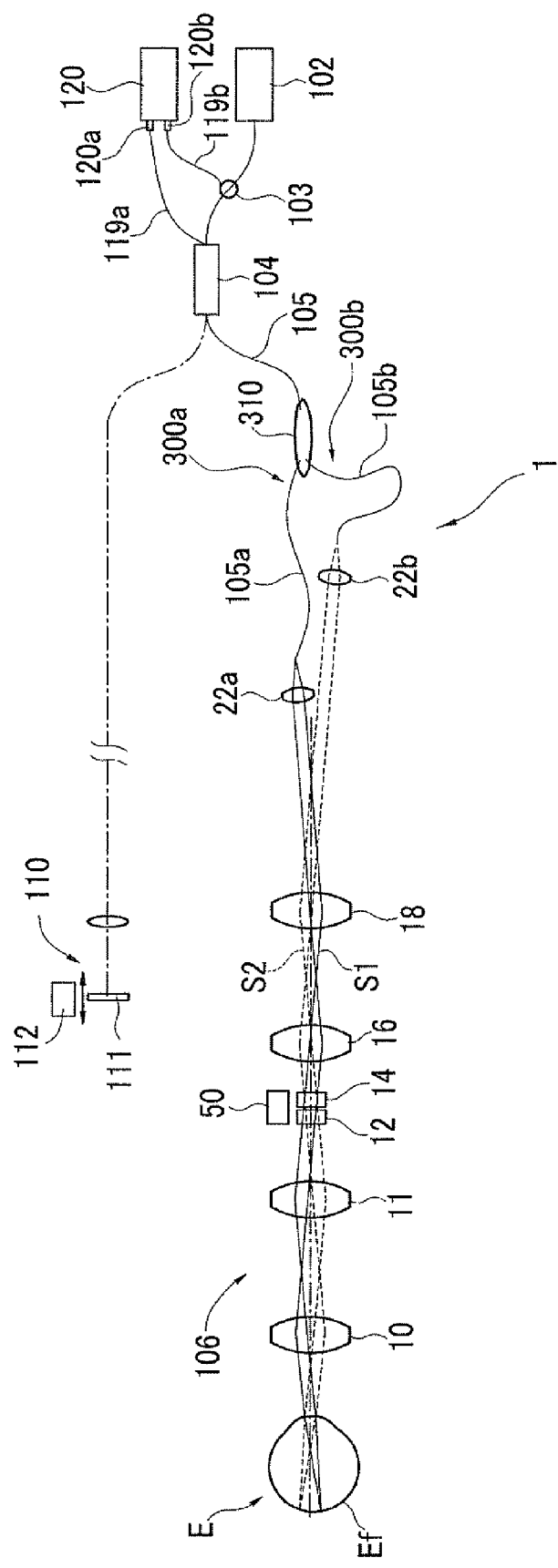
FIG. 6 schematically illustrates structural elements of an optical coherence tomography apparatus according to Example 2.

FIG. 6 is an illustration of Example 2 of the invention. The structural elements illustrated with the same reference symbols of FIG. 1 are structurally and functionally similar to those of FIG. 1. In FIG. 6, the optical delay path 300 includes a coupler 310, a first optical fiber 105a, and a second optical fiber 105b. The coupler 310 is provided in a measurement optical path to split measurement light emitted from the light source 102 into the reference optical path 300a (the first measurement optical path) and the detour optical path 300b (the second measurement optical path). The measurement light is thus split by the coupler 310 into a first measurement light S1 and a second measurement light S2. The first measurement light enters the focus lens 18 through the first optical fiber 105a and a first collimator lens 22a. The second measurement light enters the focus lens 18 through the second optical fiber 105b and a second collimator lens 22b.

Figure 5:
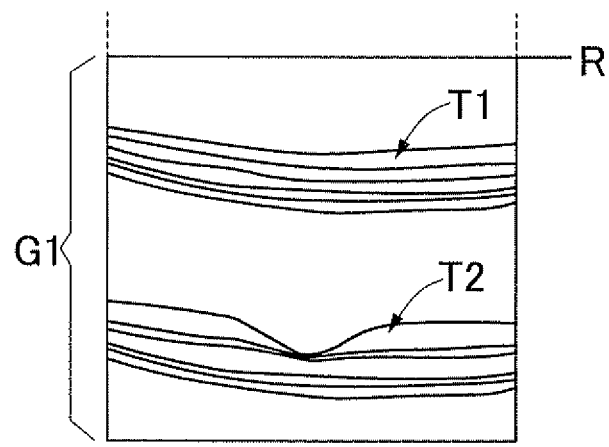
FIG. 5 illustrates a tomographic image obtained by such a dual scan as illustrated in FIG. 4.

In FIG. 6, the first optical fiber 105a and the second optical fiber 105b have an equal length. An end portion of the first optical fiber 105a on a side close to the eye E and the first collimator lens 22a, and an end portion of the second optical fiber 105 on a side close to the eye E and the second collimator lens 22b are respectively provided at different positions in an optical axis direction. This generates an optical delay (an optical path length difference) of the second measurement light in air as compared to the first measurement light S1. Accordingly, the tomographic image T1 based on the first measurement light S1 and the tomographic image T2 based on the second measurement light S2 are obtained in different regions in the depth direction as illustrated in FIGS. 3 and 5. The light advances thereafter similarly to the illustration of FIG. 1, which will not be described again.

When the first measurement light S1 and the second measurement light S2 are spatially split from each other, a Wollaston polarizing prism may be used as a light splitter. The Wollaston polarizing prism is a polarizing prism including two prisms joined with each other, wherein light perpendicularly entering therethrough is split by the two prisms into polarized lights orthogonal to each other and emitted in different directions.

The optical path length difference generated by the optical delay path 300 may be variable. In the illustration shown in FIG. 1, for example, optical distances of the first light reflector 304 and the second light reflector 306 to the light splitter 302 and the optical combiner 308 are adjusted. In the illustration shown in FIG. 6, relative positions of the first optical fiber 105a and the second optical fiber 105b in the optical axis direction may be adjusted.

The aforementioned description is based on SS-OCT, however, the technical method described so far is applicable to SD-OCT as well (spectral domain OCT). The SD-OCT uses a broad band light source (a low coherent light source) as a light source and a spectrometer (for example, a grating and line sensor) as a detector, wherein the spectrometer preferably has a high resolution to ensure an image capturing range in the depth direction.

Second Embodiment

Figure 7:
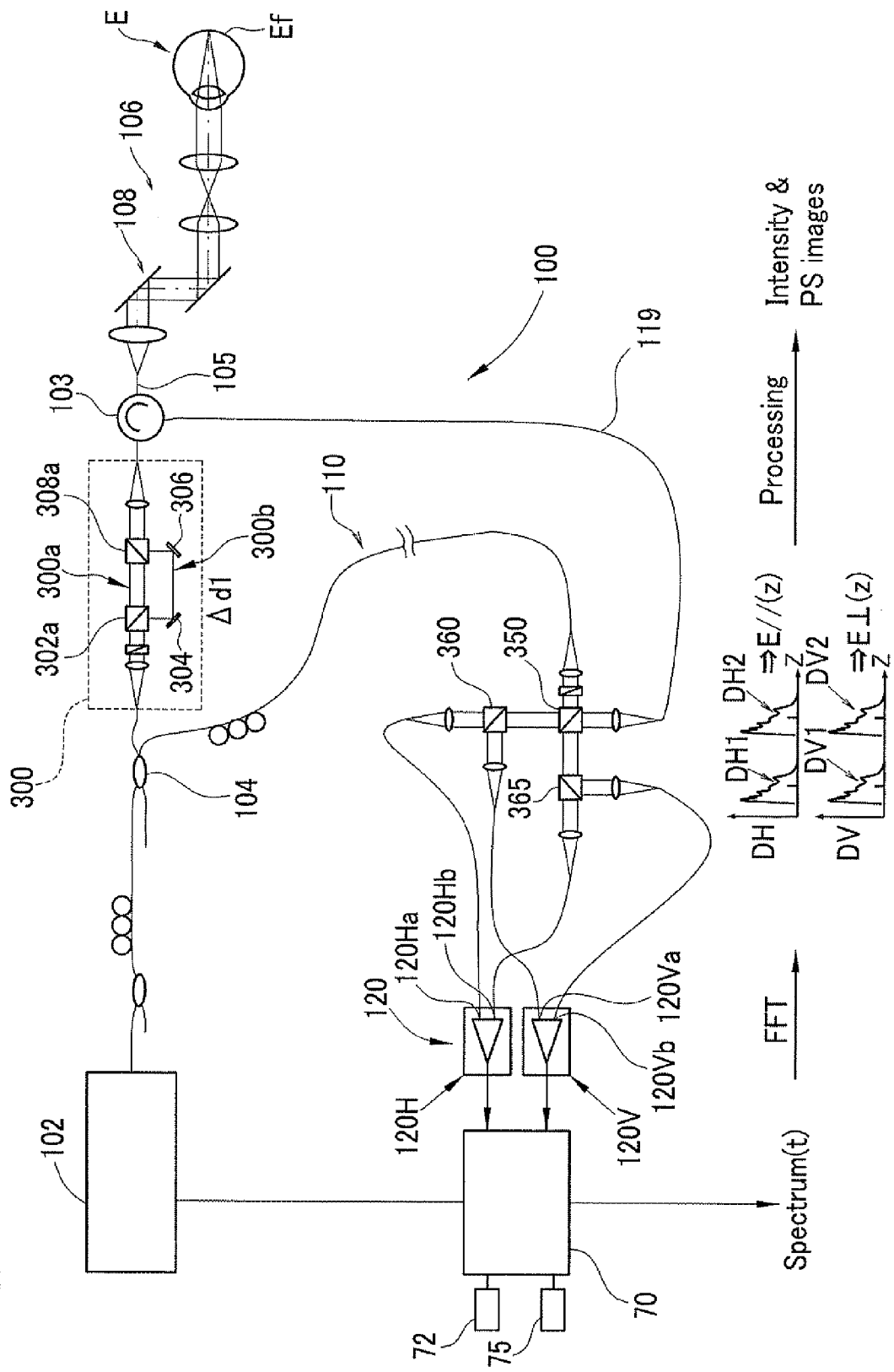
FIG. 7 is a diagram for describing the structural elements of the apparatus according to Example 1 of another embodiment.
Figure 10:
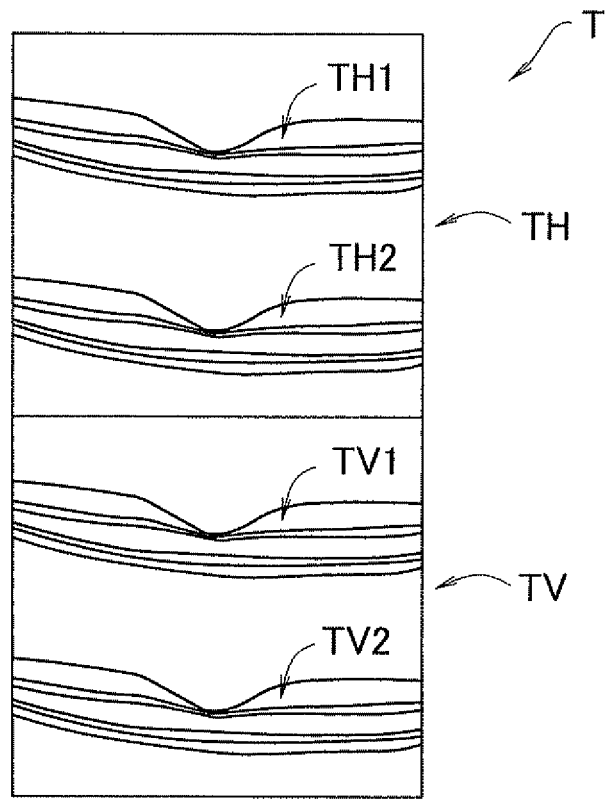
FIG. 10 illustrates an example of tomographic image data obtained based on a multiplexed spectral signal.
Figure 11:
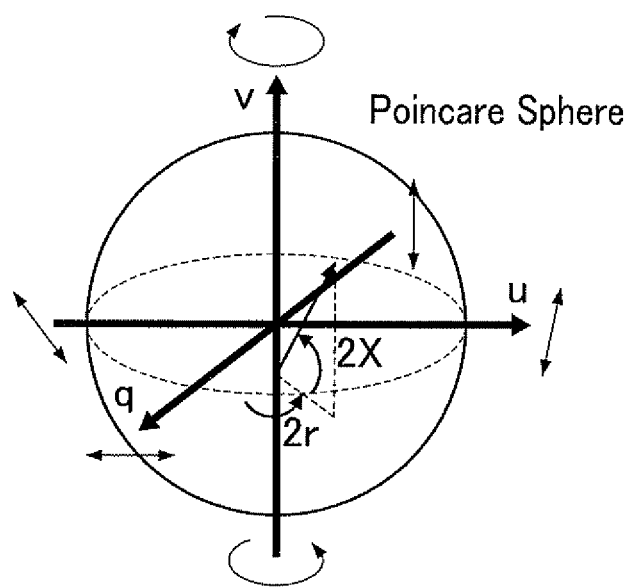
FIG. 11 is a diagram for describing Poincare Sphere according to the embodiment.
Figure 12A:
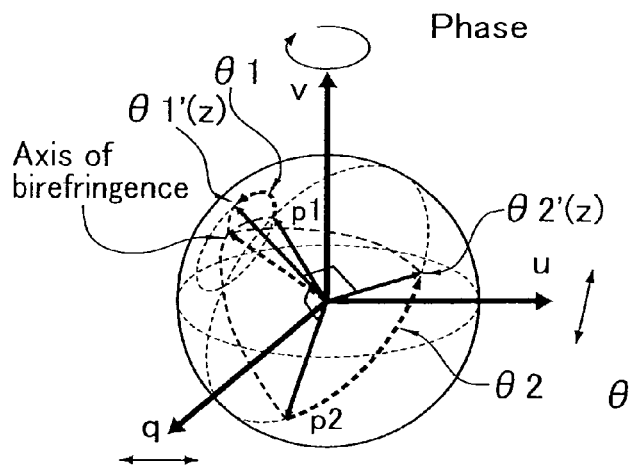
FIGS. 12A and 12B are diagrams for describing a vector A of axis of birefringence according to the embodiment.
Figure 12B:
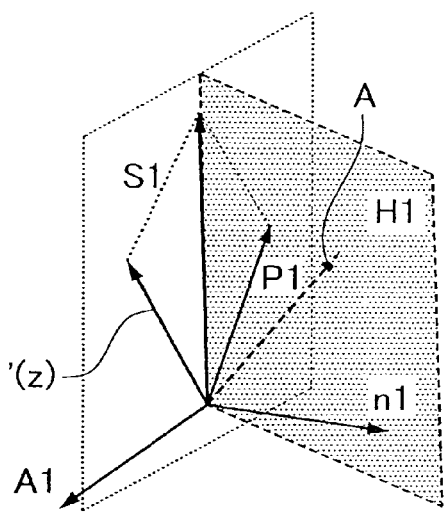
Figure 13:
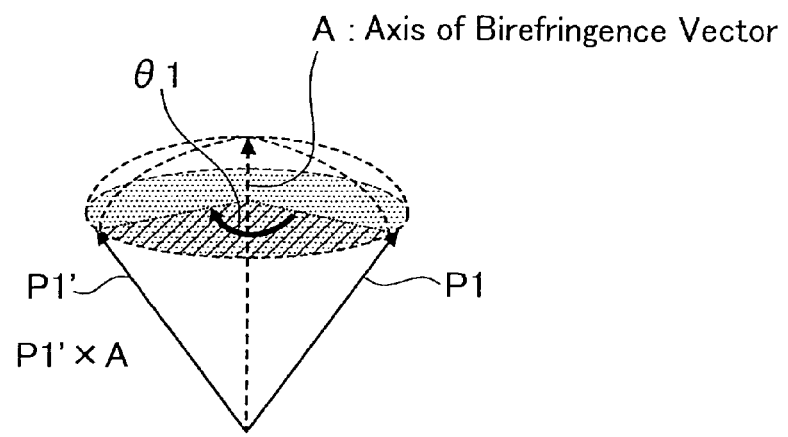
FIG. 13 is a diagram for describing Phase Retardation according to the embodiment.

A second embodiment of the invention is described referring to the drawings. FIGS. 7 and 8 are illustrations according to Example 1 of the present embodiment, and FIGS. 9 and 10 are illustrations according to Example 2 of the present embodiment. FIGS. 11 to 13 are illustrations of examples for obtaining polarization properties according to the present embodiment.

BRIEF DESCRIPTION

An optical coherence tomography apparatus of the second embodiment is briefly described below.

The apparatus has an OCT interferometer provided with an optical delay path and detects light, in which first and second spectrums having an optical path length difference therebetween are multiplexed, using a light detector. The apparatus processes an interference signal output from the detector to obtain image data including a plurality of tomographic images of an object to be examined separately obtained in the depth direction. For example, the image data includes at least two tomographic images of the object to be examined at the same image capturing position.

<Basic Configuration>

A basic configuration of an OCT apparatus 1 is Fourier domain optical coherence tomography (FD-OCT). The OCT apparatus 1 includes an interference optical system 100 (OCT optical system) and an arithmetic controller 70. The technology of the apparatus is applied to, for example, polarization sensitive OCT (PS-OCT). The technology is further applicable to standard OCT for detecting a reflection intensity of an object to be examined, Doppler OCT for detecting a phase state of an object to be examined, and multifunctional OCT in which PS-OCT and Doppler OCT are combined. Typical examples of the FD-OCT are swept source-OCT (SS-OCT) and spectral domain OCT (SD-OCT).

The interference optical system 100 is configured as an interferometer for obtaining tomographic images of an object to be examined based on OCT principles. The interference optical system 100 includes a splitter (a light splitter), a measurement optical path, a reference optical path, a combiner (an optical combiner), and a light detector (hereinafter, a detector) 120. The splitter splits light emitted from a wavelength variable light source into the measurement optical path and the reference optical path. Examples of the splitter and the combiner are; a beam splitter, a half mirror, a fiber coupler, and a circulator. The measurement optical path guides the light to the object to be examined. The reference optical path guides the light in the apparatus to make the light interfere with a measurement light. The combiner combines the measurement light from the measurement optical path reflected from the object to be examined with a reference light from the reference optical path (generate interference between the two lights). The detector 120 receives an interference signal light generated by the interference between the measurement and reference lights. An optical scanner 108 is provided in the measurement optical path to make the measurement light scan the object to be examined.

The arithmetic controller 70 controls the respective structural elements of the apparatus and performs image processes and computing processes. For example, the arithmetic controller 70 obtains a detection signal from the detector 120. The arithmetic controller 70 obtains and processes a spectral signal including an interference signal light by each wavelength. The arithmetic controller 70 processes the spectral signal to obtain data of the object to be examined in the depth direction (depth information).

Further, the arithmetic controller 70 arranges the depth information obtained from different positions through the measurement light scan to obtain information of the object to be examined (form information, polarization properties). The arithmetic controller 70 stores an obtained result in a memory 72 and displays the obtained result on a monitor 75 (an image display unit).

The spectral signal (spectral data) is rewritten in the form of function of wavelength $\lambda$ to be transformed into an equal-interval function $I(k)$ for wave number k ($=2\pi/\lambda$), or initially obtained as an equal-interval function $I(k)$ for wave number k (K-CLOCK). The arithmetic controller 70 performs Fourier transform to the spectral signal in wave number k space to obtain a reflectivity distribution in a depth (Z) region.

Any information after the Fourier transform is expressed in the form of a signal including a real number component and an imaginary number component in Z space. The arithmetic controller 70 calculates an absolute value of the real number component and the imaginary number component of signals in Z space to obtain an A-scan signal (value of signal intensity in the depth direction). The arithmetic controller 70 arranges the A-scan signals obtained from different positions to obtain a tomographic image of the object to be examined.

Examples of the object to be examined are body parts such as eye (for example, anterior segment or fundus) and skin, however, the object to be examined is not necessarily limited to such biological objects.

<Spectrum Multiplexing Technique>

The interference optical system 100 of the present embodiment is provided with optical delay paths 300 and 320 to generate at least two lights having an optical path length difference therebetween. The optical delay paths each have a reference optical path and a detour optical path. The optical delay paths are disposed in at least one of the measurement optical path and the reference optical path.

The optical delay paths 300 and 320 each have a light splitter and an optical combiner. The light splitter splits the optical path into the reference optical path and the detour optical path. The optical combiner combines the reference optical path and the detour optical path. The optical path length difference is generated by the optical delay paths so that the tomographic image obtained by one of the lights is formed in a front-side part and the tomographic image obtained by the other light is formed in a rear-side part in a tomographic image capturing range in the depth direction. Examples of the optical combiner and light splitter used in the optical delay paths are; a half mirror, a beam splitter (such as a polarization beam splitter), a fiber coupler, and a circulator.

The optical path length difference in the measurement light or the reference light generated by the optical delay path 300, 320 consequently generates a plurality of interference signal lights having an optical path length difference therebetween. The interference signal lights generated from the interference between the measurement and reference lights includes a first interference signal light based on the reference optical path and a second interference signal light based on the detour optical path. When a polarization light splitter (for example, a polarization beam splitter) is provided in each of the optical delay paths 300 and 320, a plurality of interference signal lights for different polarization states can be obtained.

The interference signal lights by different wavelengths are received and detected by the detector 120 as spectral signals. The light detector 120 detects a spectral signal in which first and second spectral signals respectively having an optical path length difference therebetween are multiplexed. The first spectral signal includes the first interference signal lights by different wavelengths, and the second spectral signal includes the second interference signal lights by different wavelengths. In the first spectrum signal and the second spectrum signal, because of the optical path length difference, interference fringes spectrally formed have different crude densities. The polarization light splitters provided in the optical delay paths 300 and 320 (for example, polarization beam splitters) enable to obtain a spectral signal in which plural spectral signals for different polarization states are multiplexed.

The arithmetic controller 70 processes the multiplexed spectral signal from the detector 120 to obtain data relating to the depth direction of the object to be examined (depth information) based on a plurality of spectral signals. The depth information includes a first depth information of the first spectral signal and a second depth information of the second spectral signal. The first depth information and the second depth information are obtained separately from each other in the depth direction. For example, the first depth information and the second depth information are obtained from the same position on the object to be examined.

For example, the arithmetic controller 70 processes the multiplexed spectral signals obtained from different positions in a transverse direction to obtain tomographic image data including a plurality of tomographic images of the object to be examined at the same time. The tomographic image data includes a first tomographic image of the first spectral signal and a second tomographic image of the second spectral signal.

First, the depth information based on the multiplexed spectral signal is useful when used to detect the polarization state of the object to be examined in PS-OCT. The apparatus of the present embodiment is not necessarily provided with, for example, an EOM in PS-OCT. Therefore, simplified and inexpensive PS-OCT can be accomplished.

Second, the depth information based on the multiplexed spectral signal including a plurality of tomographic images of the object to be examined is useful when used for image synthesis. When the depth information is thus used, synthetic images can be obtained with less time.

The arithmetic controller 70 positionally adjusts a plurality of tomographic images which are formed at different positions in the depth direction to obtain an average image. The arithmetic controller 70 can obtain an average image based on a plurality of tomographic images by using an absolute value of the real number component and the imaginary number component constituting each of the tomographic images.

The arithmetic controller 70 can obtain an average image by using the real and imaginary number components in Z space which is a basic component of each tomographic image. The arithmetic controller 70 may obtain a first average data using a signal of the real number component and a second average data using a signal of the imaginary number component and combines these data to obtain an average image based on a plurality of tomographic images.

The wavelength variable light source used in SS-OCT is advantageously a wavelength variable light source having a narrow instantaneous emission line width. When such a light source is used, two tomographic images having different optical path lengths are obtained separately from each other with an almost equal interference intensity. Further, the wavelength variable light source ensures an image capturing range including the first and second tomographic images separated from each other in the depth direction.

<Application to PS-OCT>

When the apparatus of the present embodiment is applied to PS-OCT, the optical delay paths 300 and 320 are respectively provided with devices (generator) which generate two lights having polarization components orthogonal to each other (a vertical polarization component and a horizontal polarization component). The devices may generate linearly polarized lights orthogonal to each other or may generate circularly polarized lights orthogonal to each other.

The detector 120 is provided with devices which respectively detect the vertical polarization component and the horizontal polarization component in the spectral signal. Such devices of the detector 120 may detect linearly polarized lights orthogonal to each other or may detect circularly polarized lights orthogonal to each other. The devices are, for example, a vertical polarization detector 120V which detects a vertical polarization component and a horizontal polarization detector 120H which detects a horizontal polarization component.

Preferably, the generator and the detector 120 respectively generate and detect two lights having polarization components orthogonal to each other. For example, the generator generates linearly polarized lights orthogonal to each other and the detector detects the linearly polarized lights orthogonal to each other, or the generator generates circularly polarized lights orthogonal to each other, and the detector detects the circularly polarized lights orthogonal to each other. It is unnecessary that the polarization direction of the generator or the detector match with the other.

The arithmetic controller 70 obtains polarization information (for example, birefringent index distribution) of the object to be examined based on the vertical polarization component and the horizontal polarization component in the spectral signal. For example, the arithmetic controller 70 measures the vertical polarization component in a spectral interference component using the vertical polarization detector 120V and measures the horizontal polarization component in the spectral interference component using the horizontal polarization detector 120H.

As to the vertical polarization component and the horizontal polarization component of the spectral signal, the arithmetic controller 70 obtains first depth information DV1 and DH1 of the first spectral signal and second depth information DV2 and DH2 of the second spectral signal. The first depth information and the second depth information are obtained separately from each other in the depth direction. The basic components of the first depth information and the second depth information, which are polarization components of light entering the object to be examined, are orthogonal to each other.

Two polarization states P1 and P2 are obtained from the depth information based on the multiplexed spectral signal. The polarization state P1 is obtained from a first vertical depth information DV1 ($E1\perp(z)$) obtained by the vertical polarization detector 120V and a first horizontal depth information DH1 ($E1//(z)$) obtained by the horizontal polarization detector 120H. The polarization state P2 is obtained from a second vertical depth information DV2 ($E2\perp(z)$)

obtained by the vertical polarization detector 120V and a second horizontal depth information DH2 (E2//(z)) obtained by the horizontal polarization detector 120H.

Employable methods for obtaining the polarization information are a method wherein stokes parameter is used (B. Hyle Park, M. C. Pierce, Barry Cense, S. H Yun, B. E. Bouma, J. F. de Boer, "Real-time fiber-based multi-functional spectral domain optical coherence tomography at 1.3 µm", Optics Express, Vol 13('05), pp 3931-3944), and a method wherein the known Jones vector is used (for example, see JP-A-2007-298461).

Below is described the method wherein stokes parameter is used to obtain the polarization information. It is called birefringence that there is a refraction index difference $\Delta n$ depending on directions of polarization in a material. A phase retardation 8 induced by the birefringence is expressed by distance z and wavelength $\lambda$, of light advancing in a material as follows.

$$\theta(z) = \frac{2\pi \cdot \Delta n \cdot z}{\lambda} \quad \text{(Ex. 7)}$$

The arithmetic controller 70 detects reflected light from the depth z in the object to be examined) as polarization field components E//(z) and E⊥(z) perpendicular to each other, where E⊥(z)=Re(E⊥)+jIm(E⊥)E//(z)=Re(E//)+jIm(E//). The vertical field component E⊥ is obtained from information of a real part and an imaginary part in the vertical depth information DV after the spectral signal from the vertical polarization detector 120V is subjected to Fourier analysis. The horizontal field component E//(z) is obtained from information of a real part and an imaginary part in the horizontal depth information DH after the spectral signal from the horizontal polarization detector 120H is subjected to Fourier analysis.

The arithmetic controller 70 calculates the phase retardation and birefringent axis of the sample in the form of function of the depth z from a surface of the sample and displays a calculation result on the monitor 75. It is said in fundus OCT that a nerve fiber layer is characterized by birefringence, and retinal pigment epithelium is characterized by scrambling birefringence. These characteristics help to segment and/or quantify these layers.

When the electrical field of the interference signal light is split into the polarization field components E// and E⊥ perpendicular to each other and then detected, various states of polarization are expressed by the following stokes parameter (vector) and three-dimensional display thereof, Poincare Sphere.

$$\begin{cases} I = E_{//}^2 + E_\perp^2: & \text{(i)} \\ Q = E_{//}^2 - E_\perp^2 = I\cos(2X)\cos(2\gamma): & \text{(ii)} \\ U = E_{//}E_\perp^* + E_{//}^*E_\perp = I\cos(2X)\sin(2\gamma): & \text{(iii)} \\ V = i(E_{//}E_\perp^* - E_{//}^*E_\perp) = I\sin(2X): & \text{(iv)} \end{cases} \quad \text{(Ex. 8)}$$

$$\Rightarrow p = \begin{pmatrix} q \\ u \\ v \end{pmatrix} = \begin{pmatrix} Q/I \\ U/I \\ V/I \end{pmatrix} \ldots \text{stokes parameter}$$

(i) Intensity
(ii) Difference between 0° and 90° linear polarization intensities
(iii) Difference between 45° and −45° linear polarization intensities
(iv) Difference between clockwise and anticlockwise circularly polarization intensities, where $\gamma$ represents an azimuth of elliptical polarization, and x represents an ellipticity defined by the following operational expression.

$$\frac{E_\perp}{E_{//}} = \tan X \quad \text{(Ex. 9)}$$

Describing a point on Poincare Sphere, longitude represents twice of the azimuth, and latitude represents twice of the ellipticity.

Expressing the polarization state, qu plane (equator): linear polarization, v axis: circularly polarization, qu plane to v axis: elliptical polarization, and two symmetrical points on Poicare Sphere: polarization states perpendicular to each other (see FIG. 11).

Further, the following operational expression is defined.

$$\begin{cases} \sqrt{q^2 + u^2 + v^2}: & \text{(i)} \\ \sqrt{q^2 + u^2}: & \text{(ii)} \\ v: & \text{(iii)} \end{cases} \quad \text{(Ex. 10)}$$

(i) Degree of polarization (partial polarization when <1)
(ii) Degree of linear polarization
(iii) Degree of circularly polarization Assuming that the two polarization states P1 and P2 are respectively P1'(z) and P2'(z) in the depth z on a reference surface of the sample, points P1 and P1'(z), and P2 and P2'(z) are on a circumference (dotted line) of circle whose center axis is an vector A of axis of birefringence on Poincare Sphere, and an equal phase retardation relative to the axial vector A is generated at the respective points. The axial vector A is on a plane H1 formed by a normal vector n1 of a plane formed by vectors P1 and P1'(z) and a P1+P1'(z) summed vector S1. Similarly, the axial vector A is on a plane H2 formed by a normal vector n2 of a plane formed by vectors P2 and P2'(z) and a P2+P2'(z) summed vector S2. Therefore, the vector A can be calculated as an outer product of the normal vectors A1 and A2 of the planes H1 and H2 (see FIGS. 12A and 12B).

$$A = A1 \times A2 = \{(P1+P1') \times (P1 \times P1')\} \times \{(P2+P2') \times (P2 \times P2)\} \quad \text{(Ex. 11)}$$

Assigning the following vector operational expression to { }, $A \times (B \times C) = B(A \cdot C) - C(A \cdot B)$, the first { } can be defined as follows. (Ex. 12)

$$\begin{aligned}(P1 + P1') \times (P1 \times P1') &= P1\{(P1 + P1') \cdot P1'\} - \\ &\quad P1'\{(P1 + P1') \cdot P1\} \\ &= P1(P1 \cdot P1') + P1(P1' \cdot P1') - \\ &\quad P1'(P1 \cdot P1) - P1'(P1' \cdot P1) \\ &= (P1 - P1') \cdot (P1 \cdot P1') + \\ &\quad |P1|^2(P1 - P1') \because (P1 \cdot P1) = \\ &\quad (P1' \cdot P1') = |P1|^2 \propto P1 - P1'\end{aligned} \quad \text{(Ex 13)}$$

Therefore, the axial vector A is rewritten in the following simple equation.

$$A=(P1-P1')\times(P2-P2') \quad \text{(Ex. 14)}$$

After the vector A of axis of birefringence is calculated, the phase retardation can be calculated by an operational expression of an vector inner product as follows (see FIG. 13).

$$\begin{cases} \theta 1 = \cos^{-1}\left\{\frac{(P1\times A)\cdot(P1'\times A)}{|P1\times A||P1'\times A|}\right\} \\ \theta 2 = \cos^{-1}\left\{\frac{(P2\times A)\cdot(P2'\times A)}{|P2\times A||P2'\times A|}\right\} \end{cases} \quad \text{(Ex. 15)}$$

The phase retardation is calculated for P1 and P2, however, the phase retardations calculated for P1 and P2 is generally equal. Therefore, an average value is obtained. Roughly describing the flow of the method, the axis of birefringence is first calculated, and the phase retardation is then calculated.

When the polarization information of the object to be examined is obtained as described so far, it is unnecessary to provide EOM.

The controller 70 may obtain a polarization depth information image based on the polarization information thus obtained. The controller 70 may sequentially obtain a plurality of polarization depth information images to obtain an average image of the obtained polarization depth information images. The arithmetic controller 70 can obtain an average image of the obtained polarization depth information images by using a real component and an imaginary component in the Z space which are basic components of the respective polarization depth information images.

Hereinafter, Examples of the apparatus of the present embodiment are described referring to the accompanied drawing.

Example 1

The optical coherence tomography apparatus used in Example 1 is the OCT apparatus 1 illustrated in FIG. 7, and the object to be examined is a fundus of an eye. The apparatus of Example 1 is designed to detect polarization components of an interference signal orthogonal to each other using different detectors.

The optical coherence tomography (OCT) apparatus 1 is basically configured as Swept Source-OCT (SS-OCT Hwep T Hource-OCT) and includes a wavelength variable light source 102, the interference optical system (OCT optical system) 100, and the arithmetic controller 70. The OCT apparatus 1 further includes the memory 72, the monitor 75, and a front observation system and a fixation target projection system not illustrated in the drawings. The arithmetic controller (hereinafter, controller) 70 is connected to the wavelength variable light source 102, interference optical system 100, memory 72, and monitor 75.

The OCT optical system 100 employs SS-OCT, wherein a wavelength variable light source capable of high-speed change of an emission wavelength with less time (wavelength scan light source) is used as the light source 102. The light source 102 includes, for example, a laser medium, a resonator, and a wavelength selective filter. Examples of the wavelength selective filter are a combination of a diffraction grating and a polygonal mirror, and a filter in which Fabry-Perot etalon is used.

This Example uses a tunable laser supplied by AXSUN TECHNOLOGIES INC. which is a light source having a short instantaneous emission line width and a short cavity length (for example, $\lambda c=1060$ nm, $\Delta\lambda=110$ nm, $\delta\lambda=0.055$ nm, cavity length up to 14 mm). An example of the wavelength variable light source is disclosed in US Patent Publication No. 2009/0059971.

A coupler (splitter) 104 is used as a light splitter to split light emitted from the light source 102 into a measurement light and a reference light. A circulator 103 guides the light emitted from the coupler 104 to an optical fiber 105 and guides the light from the optical fiber 105 to an optical fiber 119. A coupler may be used as the circulator 103.

The OCT optical system 100 guides the measurement light to fundus Ef of eye E using a measurement optical system 106. The OCT optical system 100 guides the reference light to a reference optical system 110. The OCT optical system 100 makes the detector (photo detector) 120 receive an interference signal light obtained by interference between the measurement light reflected from the fundus Ef and the reference light.

The measurement optical system 106 includes the optical delay path 300, the optical fiber 105, an optical scanner 108, and an objective lens system.

The optical delay path 300 includes a reference optical path 300a and a detour optical path 300b to generate at least two lights having an optical path length difference therebetween. When, for example, the optical delay path 300 is provided in the measurement optical path, at least two measurement lights having an optical path length difference therebetween are formed by the reference optical path 300a and the detour optical path 300b formed in the optical delay path 300. Because the detour optical path 300b has an optical path longer than that of the reference optical path 300a, the measurement light passing through the detour optical path 300b has an optical delay to the measurement light passing through the reference optical path (optical path length difference). A plurality of measurement lights thus respectively having different optical path lengths are irradiated on the same position of the object to be examined.

The optical delay path 300 includes a first polarization beam splitter 302a, a first light reflector 304, a second light reflector 306, and a second polarization beam splitter 308a, wherein the measurement light is split into two optical paths to delay the optical length of one of the measurement lights relative to the other. The first polarization beam splitter 302a splits the measurement light from the light source 102 into the reference optical path 300a (the first measurement optical path) and the detour optical path 300b (the second measurement optical path). The second polarization beam splitter 308a combines the reference optical path 300a and the detour optical path 300b (see FIG. 7).

Examples of the first light reflector 304 and the second light reflector 306 are optical devices such as a total reflection mirror or a prism. Describing an optical layout of the optical devices constituting the optical delay path 300, the optical devices may be provided distant from one another as illustrated in FIG. 7, or may be integrally provided by, for example, a prism.

The first polarization beam splitter 302a splits the light from the light source 102 into a vertical polarization component and a horizontal polarization component and transmits the light of one of the polarization components therethrough, while reflecting the light of the other polarization component. The first light reflector 304 and the second light reflector 306 reflect one of the lights split by the first polarization beam splitter 302a, while making the light return to the second polarization beam splitter 308a. The second polarization beam splitter 308a is characterized by combining the light split into vertically and horizontally polarized lights. After these lights are combined by the second polarization beam splitter 308a, two measurement lights having polarization components orthogonal to each other are consequently irradiated on the eye to be examined (though the polarization components of the two measurement lights are variable under the influence of the optical fiber 105, the polarization components remain orthogonal to each other).

As described so far, the optical delay path 300 generates two measurement lights having polarization components orthogonal to each other and respectively having different optical path lengths. The two measurement lights are directed toward the optical scanner 108 through the circulator 103 and the optical fiber 105. The two measurement lights are reflected in different directions by the optical scanner 108. The lights deflected by the optical scanner 108 are converted into a collimated beam by the objective lens system and enter the eye E to be irradiated on the fundus Ef. The two measurement lights are irradiated on the same position of the fundus Ef.

The optical scanner 108 makes the measurement light scan the fundus Ef in X-Y direction (transverse direction). The optical scanner 108 is located at a position substantially conjugate with pupil. The optical scanner 108 is, for example, two galvano mirrors wherein light reflection angles are arbitrarily adjusted by a drive mechanism.

The luminous flux emitted from the light source 102 accordingly changes its reflection (travelling) direction, and the luminous flux is run on the fundus in any arbitrary directions. Examples of the optical scanner 108 are a reflector mirror (galvano mirror, polygonal mirror, resonant scanner), and an acousto-optic modulator (AOM) which changes a light travelling (deflection) direction.

The controller 70 drives the optical scanner 108 to make the measurement light scan the fundus Ef in a direction perpendicular to a depth direction of the fundus Ef (transverse direction). A back scattered light of each measurement light from the fundus Ef (reflected light) travels through the objective lens system, optical scanner 108, optical fiber 105, circulator 103, and optical fiber 119 and arrives at the beam splitter 300. Then, the back scattered light is combined by the beam splitter 350 with the reference light for optical interference.

The reference optical system 110 generates the reference light to be combined with the reflected light of the measurement light from the fundus Ef. The reference optical system 110 may be of Michelson type or Mach-Zehnder type. The reference optical system 110 includes, for example, a transmission optical system (for example, an optical fiber), wherein the light from the coupler 104 is not returned to the coupler 104 but is transmitted therethrough to be directly guided to the detector 120. Another example of the reference optical system 110 includes a reflection optical system (for example, a reference mirror), wherein the light from the coupler 104 is reflected by the reflection optical system so that the light is returned to the coupler 104 again and then guided to the detector 120.

For adjustment of the different optical path lengths of the measurement light and the reference light, the apparatus moves at least a part of the optical devices provided in the OCT optical system 100 in an optical axis direction. For example, the reference optical system 110 moves the optical devices provided in the reference optical path to adjust the different optical path lengths of the measurement light and the reference light. A technical configuration for changing the different optical path lengths may be provided in the measurement optical path. In that case, the optical devices provided in the measurement optical path (for example, an end portion of the optical fiber) are moved in the optical axis direction.

The beam splitter 350 splits the interference signal light into two optical paths. A polarization beam splitter 360 is provided in one of the optical paths split by the beam splitter 350, and a polarization beam splitter 365 is provided in the other. The polarization beam splitters 360 and 365 split the incident interference signal light into polarization components orthogonal to each other (a vertical polarization component and a horizontal polarization component).

The detector 120 has a vertical polarization detector 120V and a horizontal polarization detector 120H to separately detect the vertical polarization component and the horizontal polarization component in the spectral signal.

Advantageously, balanced detectors including first photo detectors (120Va, 120Ha) and second photo detectors (120Vb, 120Hb) respectively constitute the vertical polarization detector 120V and the horizontal polarization detector 120H. The detector 120 (balanced detector) obtains a difference between interference signals from the first photo detector and the second photo detector to reduce any unwanted noise included in the interference signals. The photo detectors are each a point sensor having just one photo detecting device, an example of which is avalanche photo diode.

The vertical polarization detector 120V detects the vertical polarization components split by the polarization beam splitters 360 and 365 in a balanced manner using the first photo detector 120Va and the second photo detector 120Vb. The horizontal polarization detector 120H detects the horizontal polarization components split by the polarization beam splitter 360 and 365 in a balanced manner using the first photo detector 120Ha and the second photo detector 120Hb.

The interference signal lights received by the vertical polarization detector 120V and the horizontal polarization detector 120H respectively include interference signal lights corresponding to two measurement lights having polarization components orthogonal to each other and different optical path lengths.

After an emission wavelength is changed by the light source 102, a corresponding interference signal light is received by the detector 120 and detected by the detector 120 as a spectral signal. The controller 70 obtains a trigger signal from the light source 102 and controls the spectral signal to be obtained and the optical scanner 108.

The spectral signals detected by the vertical polarization detector 120V and the horizontal polarization detector 120H includes a first spectral signal formed based on one of the two measurement lights irradiated on the object to be examined and having the vertical polarization component and a second spectral signal formed based on the other measurement light having the horizontal polarization component. In the first spectral signal and the second spectral signal having different optical path lengths, interference fringes spectrally formed have different crude densities.

The controller 70 processes two spectral signals having different polarization components to obtain depth information DV and DH relating to the polarization components orthogonal to each other.

The controller 70 processes the spectral signal having the vertical polarization component detected by the vertical polarization detector 120V to obtain the vertical depth information DV. The vertical depth information DV includes a first vertical depth information DV1 based on the first spectral signal and a second vertical depth information DV2 based on the second spectral signal. The first vertical depth information DV1 is depth information formed based on one of the measurement lights having polarization components orthogonal to each other. The second vertical depth information DV2 is depth information formed based on the other one of the measurement lights having polarization components orthogonal to each other.

The controller 70 processes the spectral signal having the horizontal polarization component detected by the horizontal polarization detector 120H to obtain the horizontal depth information DH. The horizontal depth information DH includes a first horizontal depth information DH1 based on the first spectral signal and a second horizontal depth information DH2 based on the second spectral signal. The first horizontal depth information DH1 is depth information formed based on one of the measurement lights having polarization components orthogonal to each other. The second horizontal depth information DH2 is depth information formed based on the other one of the measurement lights having polarization components orthogonal to each other.

<Obtaining Tomographic Image>

The controller 70 drives the optical scanner 108 to make the measurement light scan the fundus Ef in the transverse direction. The controller 70 arranges the depth information obtained from different scan positions to form a fundus tomographic image.

Figure 8A:
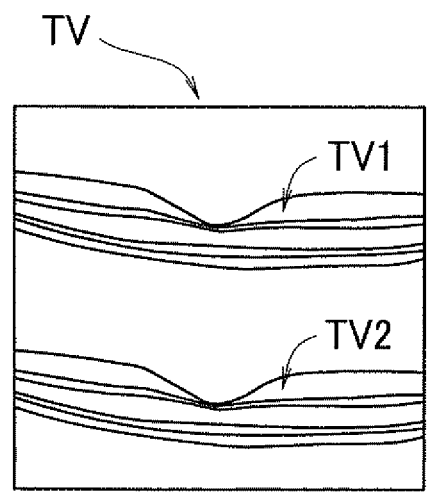
FIG. 8A illustrates an example of tomographic image data obtained based on a multiplexed spectral signal, wherein the tomographic image data relates to a vertical polarization component.
Figure 8B:
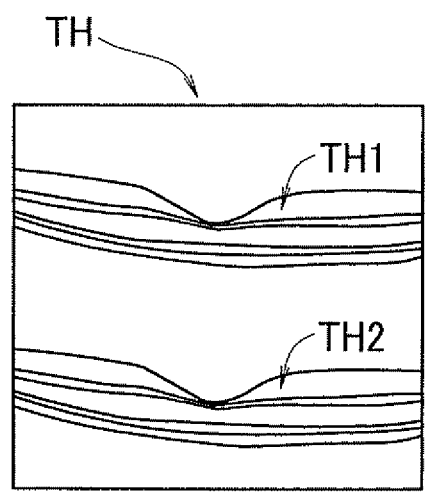
FIG. 8B illustrates an example of tomographic image data obtained based on a multiplexed spectral signal, wherein the tomographic image data relates to a horizontal polarization component.

FIGS. 8A and 8B illustrate examples of tomographic image data obtained based on a multiplexed spectral signal, wherein FIG. 8A shows tomographic image data of the vertical polarization component and FIG. 8B shows tomographic image data of the horizontal polarization component. Though a tomographic image data obtained by Fourier analysis generally includes a real image and a mirror image (imaginary image), only the real images are extracted in the illustrations of FIGS. 8A and 8B.

The controller 70 obtains tomographic image data TV and TH relating to the polarization components orthogonal to each other by arranging the depth information DV and DH relating to the polarization components orthogonal to each other in the scan direction. The tomographic image data TV and TH include a plurality of tomographic images of the fundus Ef separately obtained in the depth direction. The tomographic image data is formed by obtaining an absolute value of the real and imaginary components in the depth information. The tomographic images are obtained from the same scan position on the fundus Ef.

The tomographic image data TV includes a first vertical tomographic image TV1 based on the first vertical depth information DV1 and a second vertical tomographic image TV2 based on the second vertical depth information DV2. The tomographic image data TH includes a first horizontal tomographic image TH1 based on the first horizontal depth information DH1 and a second horizontal tomographic image TH2 based on the second horizontal depth information DH2.

The controller 70 extracts any of the first vertical tomographic image TV1, second vertical tomographic image TV2, first horizontal tomographic image TH1, and second horizontal tomographic image TH2 from the tomographic image data TV and TH thus obtained, and displays the extracted image on the display screen of the monitor 75. The controller 70 may sequentially obtain the tomographic image data TV and TH to display a moving tomographic image.

<Obtaining Average Image>

The controller 70 obtains an average image from at least two tomographic images included in the tomographic image data TV and TH. For example, the controller 70 extracts the first vertical tomographic image TV1 and the second vertical tomographic image TV2 formed at different positions in the depth direction from the tomographic image data TV. The controller 70 then positionally aligns the obtained images through image processes to obtain an average image. The controller 70 can obtain an average image from two tomographic images in the tomographic image data TH. The controller 70 may obtain an average image from the tomographic images of the tomographic image data TV and the tomographic image data TV both.

In this manner, the controller 70 can speedily obtain an average image where speckle noise is neutralized. The controller 70 may sequentially obtain the tomographic image data TV and TH and process a plurality of tomographic images included in a plurality of tomographic image data TV and TH to obtain an average image, wherein a more favorable image can be speedily obtained.

To obtain an average image, the controller 70 may obtain an average image by using the real and imaginary components in the Z space which are basic components of the tomographic images.

<Detecting Polarization>

The controller 70 obtains birefringence properties of the fundus Ef using the vertical depth information DV and the horizontal depth information DH, wherein information of the real and imaginary parts of the depth information after the spectral signal is subjected to Fourier analysis is used.

The controller 70 obtains the first vertical depth information DV1 from the vertical depth information DV and also obtains the first horizontal depth information DH1 from the horizontal depth information DH. The controller 70 obtains a first polarization state based on the first vertical depth information DV1 and the first horizontal depth information DH1 having polarization components orthogonal to each other.

The controller 70 obtains the second vertical depth information DV2 from the vertical depth information DV and also obtains the second horizontal depth information DH2 from the horizontal depth information DH. The controller 70 obtains a second polarization state based on the second vertical depth information DV2 and the second horizontal depth information DH2 having polarization components orthogonal to each other.

The controller 70 obtains birefringence properties at a position of the fundus Ef based on the first polarization state and the second polarization state, wherein a fundus surface is a reference position. The controller 70 obtains birefringence properties in the depth direction to obtain polarization depth information indicating a birefringence property distribution of the fundus Ef in the depth direction.

The controller 70 arranges the polarization depth information obtained from different positions in the scan direction to obtain the birefringence distribution of the fundus Ef on a plane in section (for example, a polarization depth information image). The controller 70 displays the obtained birefringence distribution on the monitor 75.

The controller 70 may drive the optical scanner 108 to two-dimensionally scan the fundus Ef using the measurement light, so that three-dimensional data is obtained. The controller 70 obtains the polarization depth information at different positions to obtain a two-dimensional map indicating a birefringence distribution on the fundus Ef. The controller 70 displays the obtained map on the monitor 75.

Example 2

The optical coherence tomography apparatus used in Example 2 is the OCT apparatus 1 illustrated in FIG. 9, and the object to be examined is a fundus of an eye. The apparatus of Example 2 includes a dispersive optical delay line, wherein polarization components of an interference signal orthogonal to each other may be detected by one detector. Unless stated otherwise, any structural elements illustrated with the same reference symbols are structurally and functionally similar to those of FIG. 7, and will not be described in detail again.

The first optical delay path 300 is provided in a measurement optical path formed in the interference optical system 100 to generate two measurement lights, wherein the two measurement lights have polarization components orthogonal to each other and have an equal optical path length difference $\Delta d1$ therebetween. The second optical delay path 320 is provided in a reference optical path formed in the interference optical system 100 to generate two reference lights, wherein the two reference lights have polarization components orthogonal to each other and have an equal optical path length difference $\Delta d2$ therebetween. The first optical delay path 300 and the second optical delay path 320 are basically formed from the same material except that positions they are provided and their optical path length differences are unequal.

The optical path length difference $\Delta d1$ and the optical path length difference $\Delta d2$ are set so that one of them is about twice as long as the other. In FIG. 9, $\Delta d1 > \Delta d2$, where about a half of $\Delta d1$ is equal to $\Delta d2$, however, these differences may be differently set; $\Delta d1 < \Delta d2$, where about a half of $\Delta d2$ is equal to $\Delta d1$.

A dispersive optical delay line 500 generates a wavelength-dependent phase delay and a constant group delay. The dispersive optical delay line 500 is used to double an effective image capturing region in the OCT optical system 100. A phase modulation directly exerting an action in a wave number region does not affect a laser sweep rate. For more detailed technical characteristics and operation method of the dispersive optical delay line 500, see "complete complex conjugate resolved heterodyne swept source optical coherence tomography using a dispersive optical delay line, BIOMEDICAL OPTICS EXPRESS, 1 Mar. 2012/Vol. 3. No. 3. Al-Hafeez Dhalla and Joseph A. Izatt. pp 630-632".

The detector 120 detects a vertical polarization component and a horizontal polarization component both from a spectral signal. The spectral signal includes a vertical spectral signal having the vertical polarization component and a horizontal spectral signal having the horizontal polarization component. There is an optical path length difference $\Delta d1$ between the vertical spectral signal and the horizontal spectral signal. The vertical spectral signal and the horizontal spectral signal include a first spectral signal formed based on one of the measurement lights having polarization components orthogonal to each other and a second spectral signal formed based on the other one of the measurement lights having polarization components orthogonal to each other. There is an optical path length difference $\Delta d2$ between the first spectral signal and the second spectral signal. The detector 120 (a balanced detector) obtains a difference between interference signals from a first photo detector and a second photo detector to reduce any unwanted noise included in the interference signals.

The controller 70 processes the spectral signal including the polarization components orthogonal to each other to obtain depth information. The obtained depth information D includes a vertical depth information DV and a horizontal depth information DH. The vertical depth information DV and the horizontal depth information DH are obtained separately from each other by the optical path length difference $\Delta d1$.

The vertical depth information DV includes a first vertical depth information DV1 based on the first spectral signal and a second vertical depth information DV2 based on the second spectral signal. The first vertical depth information DV1 was formed from one of the measurement lights having polarization components orthogonal to each other, and the second vertical depth information DV2 was formed from the other one of the measurement lights having polarization components orthogonal to each other. The first vertical depth information DV1 and the second vertical depth information DV2 are obtained separately from each other by the optical path length difference $\Delta d2$.

The horizontal depth information DH includes a first horizontal depth information DH1 obtained from the first spectral signal and a second horizontal depth information DH2 obtained from the second spectral signal. The first horizontal depth information DH1 was obtained from one of the measurement lights having polarization components orthogonal to each other, and the second horizontal depth information DH2 was formed from the other one of the measurement lights having polarization components orthogonal to each other. The first horizontal depth information DH1 and the second horizontal depth information DH2 are obtained separately from each other by the optical path length difference $\Delta d2$.

<Obtaining Tomographic Image>

The controller 70 drives the optical scanner 108 to make the measurement light scan the fundus Ef in the transverse direction. The controller 70 arranges the depth information obtained from different scan positions to form a fundus tomographic image.

FIG. 10 illustrates an example of tomographic image data obtained based on a multiplexed spectral signal. The controller 70 arranges depth information D in the scan direction to obtain a tomographic image data T resulting from the polarization components orthogonal to each other. The tomographic image data T includes a plurality of tomographic images of the fundus Ef separately obtained in the depth direction. The tomographic image data is formed by calculating an absolute value of the real and imaginary components of the depth information. The tomographic images were obtained from the same scan position on the fundus Ef.

The tomographic image data T includes a first vertical tomographic image TV1 based on the first vertical depth information DV1, a second vertical tomographic image TV2 based on the second vertical depth information DV2, a first horizontal tomographic image TH1 based on the first horizontal depth information DH1, and a second horizontal tomographic image TH2 based on the second horizontal depth information DH2.

The controller 70 extracts any of the first vertical tomographic image TV1, second vertical tomographic image TV2, first horizontal tomographic image TH1, second horizontal tomographic image TH2 from the tomographic image data T thus obtained and displays the extracted image on the display screen of the monitor 75. The controller 70 may sequentially obtain the tomographic image data TV and TH to display a moving tomographic image.

<Obtaining Average Image>

The controller 70 obtains an average image from at least two tomographic images included in the tomographic image data T. For example, the controller 70 extracts the first vertical tomographic image TV1 and the second vertical tomographic image TV2 formed at different positions in the depth direction from the tomographic image data T. The controller 70 then positionally aligns the obtained images through image processes to obtain an average image. The controller 70 can obtain an average image from at least two tomographic images.

In this manner, the controller 70 can speedily obtain an average image where speckle noise is neutralized. The controller 70 may continuously obtain the tomographic image data T and process a plurality of tomographic images included in a plurality of tomographic image data T to obtain an average image, wherein a more favorable image can be speedily obtained.

To obtain an average image, as described above, the controller 70 may obtain an average image by using the real and imaginary components in the Z space which are basic components of the tomographic images.

<Detecting Polarization>

The controller 70 obtains birefringence properties of the fundus Ef using the vertical depth information DV and the horizontal depth information DH included in the depth information D, wherein information of the real and imaginary parts of the depth information after the spectral signal is subjected to Fourier analysis is used.

The controller 70 obtains the first vertical depth information DV1 from the vertical depth information DV and also obtains the first horizontal depth information DH1 from the horizontal depth information DH. The controller 70 obtains a first polarization state based on the first vertical depth information DV1 and the first horizontal depth information DH1 having polarization components orthogonal to each other.

The controller 70 obtains the second vertical depth information DV2 from the vertical depth information DV and also obtains the second horizontal depth information DH2 from the horizontal depth information DH. The controller 70 obtains a second polarization state based on the second vertical depth information DV2 and the second horizontal depth information DH2 having polarization components orthogonal to each other.

The controller 70 obtains birefringence properties at a position of the fundus Ef based on the first polarization state and the second polarization state, where a fundus surface is a reference position. The controller 70 obtains birefringence properties in the depth direction to obtain polarization depth information indicating a birefringence property distribution of the fundus Ef in the depth direction.

The controller 70 arranges the polarization depth information obtained from different positions in the scan direction to obtain a birefringence distribution of the fundus Ef on a plane in section (for example, a polarization depth information image). The controller 70 displays the obtained birefringence distribution on the monitor 75.

The controller 70 may drive the optical scanner 108 to two-dimensionally scan the fundus Ef using the measurement light, so that three-dimensional data is obtained. The controller 70 obtains the polarization depth information at different positions to obtain a two-dimensional map indicating a birefringence distribution on the fundus Ef. The controller 70 displays the obtained map on the monitor 75.

According to Examples 1 and 2, the polarization beam splitter generates the polarization components orthogonal to each other, however, these Examples are not necessarily limited thereto.

For example, a half mirror which splits an optical path may be provided, wherein a polarization filter is provided in each of the optical paths split by the half mirror. The polarization properties of light selectively transmitted through the polarization filters disposed in the optical paths are set so that the polarization components are orthogonal to each other in the split optical paths.

For example, a polarization maintaining fiber may be provided. An example of the polarization maintaining fiber is PANDA fiber. When the polarization maintaining fiber is used, there is an optical path length difference between the light of one of the polarization components orthogonal to each other and the light of the other one of the polarization components because of different refraction indices for different polarization components. Therefore, a polarization maintaining fiber having such a length that generates a given optical path length difference (for example, $\Delta d1$, M2) is provided in the measurement optical path, so that two lights having a given optical path length difference therebetween are generated. Such a polarization maintaining fiber is coupled with a conventional single mode fiber through the coupler, or the polarization maintaining fiber may be provided as a fiber to be disposed between the circulator and the eye.

The optical coherence tomography apparatus of the present embodiment can be expressed as described as follows.

A first optical coherence tomography apparatus includes a light source, an interferometer, and a photo detector, wherein a spectral signal from the detector is processed to obtain depth information of an object to be examined, the apparatus further including: a first technical configuration for generating a plurality of lights having an optical path length difference therebetween; and a second technical configuration for obtaining a multiplexed spectral signal including interference signal components by wavelengths in which a first spectral signal and a second spectral signal generated by the first technical configuration are multiplexed. The apparatus thus technically characterized obtains depth information in which plural depth information separately obtained in a depth direction are multiplexed.

A second optical coherence tomography apparatus has a unit for generating an optical delay difference in at least one of a measurement optical path (sample arm) and a reference optical path (reference arm), wherein a technical configuration for multiplexing a plurality of OCT images along a depth axis is provided.

A third optical coherence tomography apparatus measures a plurality of times a multiplexed OCT image obtained in one measurement and positionally aligns the obtained images to obtain an average image, or obtains an average image per real part or imaginary part and then obtains an OCT image representing an absolute value.

A fourth optical coherence tomography apparatus is characterized in that an optical delay difference is generated in the polarization components perpendicular to each other, and two multiplexed OCT images are obtained by two photo detectors by each of components perpendicular to each other after the measurement light (sample light) and the reference light are combined to interfere with each other. The apparatus then analyzes the polarization of an object to be examined.

A fifth optical coherence tomography apparatus has units for generating an optical delay difference in the polarization components perpendicular to each other each provided in the reference optical path and the measurement optical path, and four multiplexed OCT images are obtained by one photo detector to analyze polarization of the object to be examined.

A sixth optical coherence tomography apparatus is any of the first to fifth optical coherence tomography apparatuses wherein a full range unit is further provided to facilitate multiplexing. Examples of the full range unit are DODL, phase shift unit (for example, a mirror provided in the measurement optical path or the reference optical path, a mechanism for finely moving an optical device such as an optical fiber by using a piezoelectric element), and optical modulation unit (for example, EO modulator which modulates the measurement light or the reference light). When the phase shift or optical modulation is performed, the controller may perform the phase shift or optical modulation at a scan position and change the scan position in B scan. The controller may perform the phase shift or optical modulation while changing the scan position in B scan.

A seventh optical coherence tomography apparatus is any of the fourth to sixth optical coherence tomography apparatuses wherein the polarization is analyzed after OCT images having four different polarization states are each averaged (for example, per real part or imaginary part).

REFERENCE SIGNS LIST

1 Optical coherence tomography (OCT) apparatus
70 Arithmetic controller
100 Interference optical system (OCT optical system)
102 Wavelength variable light source
104 Coupler
106 Measurement optical system
108 Optical scanner
110 Reference optical system
120 Detector
300 Optical delay path
120V Vertical polarization detector
120H Horizontal polarization detector
320 Second optical delay path
500 Dispersive optical delay line

The invention claimed is:

1. An optical coherence tomography apparatus comprising:
an optical coherence tomography optical system comprising:
a measurement optical path,
a reference optical path,
an optical path length difference generator placed in at least one of the measurement optical path and the reference optical path and configured to generate at least two lights having an optical path length difference from each other, the generator comprising,
a light splitter configured to split at least one of the measurement optical path and the reference optical path into a first optical path and a second optical path that is a detour optical path, and
an optical combiner configured to combine the first optical path and the second optical path, and
a detector configured to obtain a multiplexed spectral interference signal in which a first spectral interference signal and a second spectral interference signal based on the at least two lights generated by the optical path length difference generator are multiplexed, and
an arithmetic controller configured to process the multiplexed spectral interference signal output from the detector to obtain depth information in which first depth information based on the first spectral interference signal and second depth information based on the second spectral interference signal are multiplexed separately from each other in a depth direction,
the first depth information and the second depth information being depth information at a same depth position on an object to be examined and are obtained simultaneously.

2. The optical coherence tomography apparatus according to claim 1, further comprising an optical scanner placed in the measurement optical path, and
wherein the arithmetic controller processes the depth information obtained at each scan position by the optical scanner to obtain tomographic image data including a plurality of tomographic images on the object at the same time.

3. The optical coherence tomography apparatus according to claim 1, wherein the arithmetic controller positionally aligns and combines the first depth information and the second depth information in the depth direction.

4. The optical coherence tomography apparatus according to claim 1, wherein the arithmetic controller obtains a plurality of the first depth information and the second depth information and positionally aligns and combines the first depth information and the second depth information in the depth direction.

5. The optical coherence tomography apparatus according to claim 1, wherein
the optical path length difference generator is configured to generate at least two lights having polarization components orthogonal to each other and to generate at least two lights having an optical path length difference therebetween and having polarization components orthogonal to each other,
the detector is a detector configured to detect at least two multiplexed spectral interference signals having polarization components orthogonal to each other, and
the arithmetic controller processes at least two multiplexed spectral interference signals having polarization components orthogonal to each other to analyze polarization properties of the object to be examined.

6. The optical coherence tomography apparatus according to claim 1, wherein the detector includes a vertical polarization detector for detecting a multiplexed spectral interference signal having a vertical polarization component and a horizontal polarization detector for detecting a multiplexed spectral interference signal having a horizontal polarization component.

7. The optical coherence tomography apparatus according to claim 1, further comprising a full range unit placed in one of the measurement optical path and the reference optical path and configured to obtain a full-range image capturing region in the depth direction.

8. The optical coherence tomography apparatus according to claim 1, wherein
the optical path length difference generator is placed in the measurement optical path, and
the optical coherence tomography optical system further comprises a scan optical system configured to simultaneously scan the at least two lights having an optical path length difference from each other at a same depth position on the object to be examined in a transverse direction.

9. The optical coherence tomography apparatus according to claim 8, wherein the scan optical system is a scan optical system configured to scan the at least two lights having an optical path length difference from each other at a same scanning position on the object to be examined.

10. The optical coherence tomography apparatus according to claim 8, wherein the scan optical system is a scan optical system which scans the at least two lights having an optical path length difference from each other at different positions on the object to be examined.

11. The optical coherence tomography apparatus according to claim 1, wherein the object to be examined is a fundus of an eye.

12. The optical coherence tomography apparatus according to claim 1, wherein
the optical coherence tomography optical system is a swept source OCT optical system, and
the detector is a balanced detector including at least two point sensors.

13. The optical coherence tomography apparatus according to claim 1, wherein the arithmetic controller measures a variation between the first depth information and the second depth information.

14. The optical coherence tomography apparatus according to claim 1, wherein the optical coherence tomography optical system is a spectral-domain-optical coherence tomography (SD-OCT) system.

15. The optical coherence tomography apparatus according to claim 1, wherein at least one of the first optical path and the second optical path in the optical path length difference generator includes an optical fiber.

16. An optical coherence tomography apparatus comprising:
an optical coherence tomography optical system comprising:
a measurement optical path,
a reference optical path,
an optical path length difference generator placed in the measurement optical path and configured to generate at least two lights having an optical path length difference from each other, the generator being configured to produce a first optical path and a second optical path that is a detour optical path,
an optical scanner placed on a side closer to the object than the optical path length difference generator, and
a detector configured to obtain a multiplexed spectral interference signal in which a first spectral interference signal and a second spectral interference signal generated by the optical path length difference generator are multiplexed, and
an arithmetic controller configured to process the multiplexed spectral interference signal output from the detector to obtain depth information in which first depth information based on the first spectral interference signal and second depth information based on the second spectral interference signal are multiplexed separately from each other in a depth direction,
the first depth information and the second depth information being depth information at a same depth position on an object to be examined and are obtained simultaneously.

17. The optical coherence tomography apparatus according to claim 16, wherein the arithmetic controller processes the depth information obtained at each scan position by the optical scanner to obtain tomographic image data including a plurality of tomographic images on the object at the same time.

18. The optical coherence tomography apparatus according to claim 16, wherein the arithmetic controller positionally aligns and combines the first depth information and the second depth information in the depth direction.

19. The optical coherence tomography apparatus according to claim 16, wherein at least one of the first optical path and the second optical path in the optical path length difference generator includes an optical fiber.

* * * * *